US008426154B2

(12) United States Patent
Stoecker et al.

(10) Patent No.: US 8,426,154 B2
(45) Date of Patent: Apr. 23, 2013

(54) IMMUNOASSAY FOR VENOM DETECTION INCLUDING NONINVASIVE SAMPLE COLLECTION

(75) Inventors: William V. Stoecker, Rolla, MO (US); Hernan F. Gomez, Whitmore Lake, MI (US); Jonathan A. Green, Columbia, MO (US); David L. McGlasson, San Antonio, TX (US)

(73) Assignees: SpiderTech, a Division of Stoecker & Associates, a Subsidiary of The Dermatology Center, LLC., Rolla, MO (US); The Regents of the University of Michigan, Office of Technology Transfer, Ann Arbor, MI (US); The Curators of the University of Missouri, University Hall, Columbia, MO (US); The United States of America as Represented by the Secretary of the Air Force, Directorate of Intellectual Property Law, Washington, DC (US)

( * ) Notice: Subject to any disclaimer, the term of this patent is extended or adjusted under 35 U.S.C. 154(b) by 447 days.

(21) Appl. No.: 12/756,875

(22) Filed: Apr. 8, 2010

(65) Prior Publication Data

US 2010/0196938 A1    Aug. 5, 2010

Related U.S. Application Data

(62) Division of application No. 11/550,130, filed on Oct. 17, 2006, now Pat. No. 7,927,828.

(60) Provisional application No. 60/727,300, filed on Oct. 17, 2005.

(51) Int. Cl.
*G01N 33/53* (2006.01)
*G01N 33/566* (2006.01)

(52) U.S. Cl.
USPC ......... 435/7.92; 435/7.94; 436/501; 436/514; 436/518

(58) Field of Classification Search ............... None
See application file for complete search history.

(56) References Cited

U.S. PATENT DOCUMENTS

| | | |
|---|---|---|
| 3,888,629 A | 6/1975 | Bagshawe |
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 4,582,699 A | 4/1986 | Murray et al. |
| 4,707,450 A | 11/1987 | Nason ........................... 600/572 |
| 4,877,741 A | 10/1989 | Babcock et al. |
| 4,916,057 A | 4/1990 | Thompson et al. |
| 4,943,522 A | 7/1990 | Eisinger et al. |
| 4,978,504 A | 12/1990 | Nason ............................. 422/61 |
| 5,084,245 A | 1/1992 | Berke et al. |
| 5,155,022 A | 10/1992 | Naqui et al. |
| 5,163,441 A | 11/1992 | Monthony et al. |
| 5,196,193 A | 3/1993 | Carroll ........................ 424/172.1 |
| 5,208,535 A | 5/1993 | Nakayama et al. |
| 5,395,754 A | 3/1995 | Lambotte et al. |
| 5,508,171 A | 4/1996 | Walling et al. |
| 5,529,922 A * | 6/1996 | Chapman et al. ............. 435/327 |
| 5,534,132 A | 7/1996 | Vreeke et al. |
| 5,670,381 A | 9/1997 | Jou et al. |
| 5,753,262 A | 5/1998 | Wyse et al. |
| 5,916,193 A | 6/1999 | Stevens et al. ................. 604/509 |
| 5,965,453 A | 10/1999 | Skiffington et al. .......... 436/165 |
| 6,194,220 B1 | 2/2001 | Malick et al. |
| 6,241,863 B1 | 6/2001 | Mobnouquette |
| 6,248,294 B1 | 6/2001 | Nason |
| 6,270,637 B1 | 8/2001 | Crismore et al. |
| 6,281,006 B1 | 8/2001 | Heller et al. |
| 6,461,496 B1 | 10/2002 | Feldman et al. |
| 6,794,153 B2 | 9/2004 | Yi et al. |
| 2005/0136553 A1 | 6/2005 | Kaylor et al. |
| 2007/0071750 A1 | 3/2007 | Riano-Umbarila et al. |

OTHER PUBLICATIONS

Merck Manual print-out from http://www.merckmanuals.com/home/injuries_and_poisoning/bites_and_stings/snake_bites.html, retrieved on Nov. 8, 2012.*
Swanson, D.L, et al. "Bites of Brown Recluse Spiders and Suspected Necrotic Arachnidism", *N Engl J Med.* 352(7): 700-707.
Al-Thaer, F et al. "Comparison of Visual Inspection, an Allergen-specific Method ELISA) and Nonspecific methods Sensitive ATP and Total Protein) to Detect the Presence of Allergenic Food Residues on Food Contact surfaces"; 2007 Detection of dried egg residues on a stainless steel surface using ELISA and sensitive ATP www.charm.com/content/view/43/68.lang.en.

(Continued)

*Primary Examiner* — Shafiqul Haq
*Assistant Examiner* — Galina Yakovleva
(74) *Attorney, Agent, or Firm* — e winner & associates, pllc; Ellen P. Winner

(57) ABSTRACT

Methods and immunoassays for diagnosing a bite or sting of a venomous organism in a patient having symptoms consistent with such a bite or sting are provided. A sample of venom is collected from the area of the suspected bite or sting using a swab and then contacted with an antibody that specifically binds to an antigenic site on venom present in the sample. Binding is then detected. The invention is illustrated by examples showing diagnosis of brown recluse spider bite, distinguishing it from other diagnoses with which it is often confused. This extremely sensitive test can detect venom antigens down to about 20 picograms even after the sample has been shipped and stored for periods of up to three weeks during the summer.

14 Claims, 17 Drawing Sheets

OTHER PUBLICATIONS

Babcock, JL et al, (1986) "Immunotoxicology of brown recluse spider venom," *Toxicon* 24: 783-790.

Beckwith, ML et al, (1980) "Effects of antiserum on the systemic response in mice caused by a component isolated from an extract of brown recluse spider venom," *Toxicon* 18: 663-666.

Corzo, G. et al. (2000) "Isolation, synthesis and pharmacological characterization of d-palutoxins IT, novel isecticidal toxins from the spider *Paracoelotes luctuosus* (Amaurobiidae)," *Eur. J. Biochem.* 267: 450-456.

Dart, R.C. et al. (1995) "Reptile bites and scorpion stings," *Emergency Medicine: A Comprehensive Study Guide*, editors Judith E. Tintinalli, Ernest Ruiz & Ronald L. Krome, 4th ed., McGraw Hill Press, New York, pp. 864-867.

Desai, A et al. (1999) "*Laxosceles deserta Spider Venom* Induces NF-KB-Dependent Chemokine Production by Endothelial Cells," *Clinical Toxicology*, 37: 447-456.

"Doctor's downplay spider bite death," published Apr. 5, 2008, United Press International. http://UPI.com. (news item showing there's no way to diagnose brown recluse spider bite for disclosure).

Edwards, G.B. et al. (2001) "The Present Status and a Review of the Brown Recluse and Related Spiders , *Loxosceles* spp. (Araneae: Sicariidae), in Florida," *Entomology Circular* No. 406:1-6.

Gomez, H.F. et al. (1995) "Clinical Toxicology of Snakebite in North America," *Handbook of Clinical Toxicology of Animal Venoms and Poisons*, editors Jurg Meier & Julian White, CRC Press, Florida, USA, pp. 619-640.

Gomez, H. F., et al. (2001), "Direct Correlation between Diffusion of *Loxosceles reclusa* Venom and Extent of Dermal Inflammation," *Academic Emergency Medicine* 8(4):309-314.

Gomez, H.F. et al, (1994) "Human Envenomation From a Wandering Garter Snake," *Annal Emerg. Med.*, 23:1119-1122.

Gomez, HF et al. (1999) "*Loxosceles* Spider Venom Induces the Production of α and β Chemokines: Implications for the Pathologenesis of Dermonecrotic Arachnidism," *Inflammation*, 23: 207-215.

Gomez, H.F. et al. (2003) "Recluse spider and other necrotizing arachnids," *Ellenhorn's Medical Toxicology, Diagnosis and Treatment of Human Poisoning*, editor Dart R.C., Lippincott.

McGlasson, D.L. et al. (2007) "Cutaneous and Systemic Effects of Varying Doses of Brown Recluse Spider Venom in a Rabbit Model," *Clin. Lab Sci*. 2007: 20(2):99-105.

McGlasson, DL et al. (1988) "Evaluation of the lupus-like anticoagulant effect of brown recluse spider venom," *Blood* 72 (5(supl 1)): 303a (abs 1121).

McGlasson, DL et al. (1990) "Specimen processing requirements and quality control in the detection of a lupus anticoagulant," *Clin. Hemostasis Review* 4: 7-8.

Phillips, S et al. (1995) Therapy of Brown Spider Envenomation: A Controlled Trial of Hyperbaric Oxygen, Dapsone and Cyproheptadine. Annals of Emerg. Med., 25(3) 363-368.

Stoecker et al. (2006) "Diagnosis if loxocelism in a child confirmed with an enzyme-linked immunosorbent assay and noninvasive tissue sampling" *J. Am. Acad. Dermatol.*; 888-890.

Trevett, A.J. et al., (1995) "Venom Detection Kits in the Management of Snakebite In Central Province, Papus New Guinea." Toxicon. vol. 33. No. 5. pp. 703-705.

Whetstone, W.D. et al. (1997) "Inhibition of Dermonecrotic Arachnidism with Interleukin-8 Monoclonal Antibody," *Acad. Emerg. Med.*, 4:437 (abs 288).

Olvera et al., Toxicon. vol. 48. No. 1, pp. 64-74, 2006.

Tambourgi et al., Molecular Immunology, vol. 41, pp. 831-840, 2004.

Selvanayagam,Z.E. et al., Tests for Detection of Snake Venoms, Toxins and Venoms Antibodies: Review on Recent Trends (1987-1997), Toxicon, Apr. 1999; vol. 37, No. 4, pp. 565-586.

Chandler et al. (May 1982) "A New enzyme Immunoassay System Suitable for Field Use and Its Application in a Snake Venom Detection Kit," *Clin. Chim. Acta* 121(2):225-230.

CSL Antivenom Handbook, Snake Venom Detection , http://www.toxinology.com/generic_static_files/cslavh_svdk.html , Downloaded Jul. 25, 2007.

Asbell et al. (1995) "Rapid Diagnosis of Ocular Herpes Simplex Infections," *Br. J. Ophthalm*. 79(5):473-475.

Atilla et al. (2004) "Clinical Course of a *Loxosceles* Spider Bite in Turkey," *Vet. Hum. Toxicol* 46(6):306-308.

Atkins et al. (1958) "Necrotic Arachnidism," *Am. J. Med. Hyg.* 7:165-184.

Babcock et al. (1981) "Purification and Characterization of a Toxin from Brown Recluse Spider (*Loxosceles* recluse) Venom Gland Extracts," *Toxicon* 19(5):677-689.

Babcock et al. (1981) "Systemic Effect in Mice of Venom Apparatus Extract and Toxin From the Brown Recluse Spider (*Loxosceles reclusa*)," *Toxicon* 19(4):463-471.

Barbaro et al. (1992) "IgG Antibodies to *Loxosceles* sp. Spider Venom in Human Envenoming," *Toxicon* 30:1117-1121.

Barrett et al. (1993) "Passive Hemagglutination Inhibition Test for Diagnosis of Brown Recluse Spider Bite Envenomation." *Clin. Chem.* 39:2104-2107.

Berger et al. (1973) "An In Vitro Test for *Loxosceles* recluse Spider Bites," *Toxicon* 11:465-470.

Bilger, B. (Mar. 5, 2007) "Spider Woman," *The New Yorker* 66-73.

Borkan et al. (1995) "An Outbreak of Venomous Spider Bites in a Citrus Grove," *Am. J. Trop. Med. Hyg.* 52(3):225-230.

Boyer et al. (2000) "Spider on the Headboard, Child in the Unit: Severe *Loxosceles arizonica* Envenomation Confirmed by Delayed Spider Identification and Tissue Antigen Detection," *J. Tox. Clin. Tox* 38:510 Abstract.

Cacy et al. (1999) "The Clinical Characteristics of Brown Recluse Spider Bites Treated by Family Physicians: An OKPRN Study." *J. Fam. Prac.* 48:536-542.

Chavez et al. (1998) "ELISA for the Detection of Venom Antigen in Experimental and Clinical Envenoming by *Loxosceles* Intermedia Spiders," *Toxicon* 36(4):563-569.

Clowers, T.D. (1996) "Wound Assessmet of the *Loxosceles* recluse Spider Bite," *J. Emer. Nursing* 22(4):283-287.

Cole et al. (1995) "Brown Recluse Spider Envenomation of the Eyelid: An Animal Model," *Ophthal. Plast. Reconstr. Surg.* 11(3):153-164.

da Silveira et al. (2006) "Molecular Cloning and Functional Characterizzation of Two Isoforms of Dermonecrotic Toxin for *Loxosceles intermedia* (Brown Spider) Venom Gland," *Biochimia* 88:1241-1253.

Edwards et al. (1980) "Loxoscelism of the Eyelids," *Arch. Ophthalmol*. 98(11):1997-2000.

Elston et al. (May 2005) "Comparison of Colchicine, Dapsone, Triamoinolone, and Diphebhydramine Therapy for the Treatment of Brown Recluse Spider Envenomation: A Double-Blind, Controlled Study in a Rabbit Model," *Arch. Dermatol.* 141(5):595-597.

Estivill-Torrus et al. (1998) "Quantification of the Secretory Glycoproteins of the Subcommissural Organ by a Sensitive Sandwich ELISA with a Polyclonal Antibody and a Set of Monoclonal Antibodies Against the Bovine Reissner's Fiber," *Cell Tiss. Res*. 294(3):407-413.

Favre et al. (1989) "Epitope Mapping of Recombinant Human Gamma Interferon Using Monoclonal Antibodies," *Mol. Immunol.* 26(1):17-25.

FDA Advice Website, www.fda.gov/cdrh/devadvice/ide/index.shtml, Jul. 8, 2003.

Finke et al. (1974) "Serodiagnostic Test for *Loxosceles* recluse Bites," *Clin Toxicol.* 7:375-382.

Gantep Website (2006) www.gantep.edu.tr/~varol/eng/poisonous, Accessed Feb. 26, 2006.

Gomez et al. (1999) "Intradermal Anti-*Loxosceles* Fab Fragments Attenuate Dermonecrotic Arachnidism," *Academic Emerg. Med.* 6:1195-1202.

Gomez et al. (2001) "Antigenic Cross-Reactivity of Venoms from Medically Important North American *Loxosceles* Spiders Species," *Toxicon* 39(6):817-824.

Gomez et al. (May 2002) "A New Assay for the Detection of *Loxosceles* (Brown Recluse) Spider Venom," *Ann. Emerg. Med.* 39(5):469-474.

Gross et al. (1989) "Persistent Segmental Coetaneous Anesthesia after a Brown Recluse Spider Bite," *South Med J.* 83:1321-1323.

Guilherme et al (2001) "Neutralizations of Dermonecrotic and Lethal Activities and Differences Among 32-35 kDa Toxins of Medically Important *Loxosceles* Spider Venoms in Brazil Revealed by Monoclonal Antibodies," *Toxicon* 39(9):1333-1342.

Hoover et al. (1990) "Pseudoepitheliomatous Hyperplasia and Pyoderma Gangrenosum After a Brown Recluse Spider Bite," *South Med. J.* 83:243-224.

Huang et al. (2001) "Development of a Sandwich ELISA Test for Arginase Measurement Based on Monoclonal Antibodies," *Hybridoma* 20(1):53-57.

Jarvis et al. (Aug. 2000) "Brown recluse Spider to Bite the Eyelid," *Ophthalmology* 107(8):1492-1496.

Krywko et al. (2002) "Detection of *Loxosceles* Species Venom in Dermal Lesions: A Comparison of 4 Venom Recovery Methods," *Ann. Emerg. Med.* 39(5):475-480.

Maisel et al. (1994) "Cervical Necrotizing Fascitis," *Laryngoscope* 104(7):795-798.

Mcgiasson et al. (1993) "An Evaluation of a Positive Control for Platelet Neutralization Procedure testing with Seven Commercial Activated Partial Thromboplastin Time Reagents," *Am. J. Clin. Pathol.* 100(5):576-578.

Miller et al. (2000) "Detection of *Loxosceles* Venom in Lesional Hair Shafts and Skin: Application of a Specific Immunoassay to Identify Dermonecrotic Arachnidism," *Am. J. Emerg. Med.* 18:626-268.

Moaven et al. (1999) "Sporotrichosis Mimicking Necrotising Arachnidism," *Med. J. Aust.* 171:865-868.

Mold et al. (2004) "Management of Brown Recluse Spider Bites in Primary Care," *JABFP* 17(5):347-352.

Osborn et al. (1989) "Tumor Necrosis Factor and Interleukin 1 Stimulate the Human Immunodeficiency Virus Enhancer by Activation of Nuclear kB," *Proc. Nat. Acad. Sci. USA* 86:2336-2340.

Pauli et al. (2006) "The Efficacy of Antivenom in Loxoscelism Treatment," *Toxicon* 48:123-137.

Platnik, N.I. (2000) "The World Spider Catalog, Version 7.5," http://research.amnh.org/entomology/spiders/catalog/SICARIIDAE.htmlmf.

Racchetti et al. (Nov. 1987) "Production of Monoclonal Antibodies to Calcitonin and Development of a Two-Site Enzyme Immunoassay," *Mol. Immunol.* 24(11):1169-1176.

Rees et al. (1987) "The Diagnosis and Treatment of Brown Recluse Spider Bites," *Ann. Emerg. Med.* 16:945-949.

Rosenstein et al. (1987) "Lyme Disease Misdiagnosed as a Brown Spider Bite," *Ann. Inter. Med.* 107:782.

Sams et al. (2001) "Necrotic Arachnidism," *J. Am. Dermatol.* 44:561-573.

Sams et al. (2001) "Nineteen Documented Cases of *Loxosceles* recluse Envenomation," *J. Am. Acad. Dermatol.* 44:503-608.

Shenefelt, P. D. (1997) "Loxoscelism," In: *Clinical Dermatology*, Dennis, D.J. ed., ch. 18-25, Lippincott-Raven, Philadelphia, pp. 1-12.

Smith et al. (1985) "Measurement of Protein Using Bioinchonic Acid," *Anal. Biochem.* 150:76-85.

Smith et al. (1988) "Single-Step Purification of Polypeptides Expresses in *Escherichia coli* as Fusions with Glutathions S-Transferase," *Gene* 67:31-40.

Stoecker, W.V. (Oct. 1996) *Update on Computer Applications in Dermatology*, Missouri Derm. Soc., Kansas City, MO.

Tajima et al. (1998) "Production of a Monoclonal Antibody Reacted Broadly with Feline Calicvirus Field Isolates," *J. Vet. Med. Sci.* 60(2):155-160.

Taylor et al. (1966) "Hemolysis, Renal Failure and Death, Presumed Secondary to Bite of Brown Recluse Spider," *South Med. J.* 58:1209-1211.

Vetter al. (1998) "Envenomation by a Spider, *Agelenopsis aperta* (family: Agelenidae) Previously Considered Harmless," *Ann. Emerg Med.* 16:945-949.

Vetter et al. (1998) "Bites and Stings of Medically Important Venomous Arthropods," *Int. J. Dermatol.* 37:481-496.

Vetter et al. (2003) "Diagnostic Confusion in Lymphomaloid Papulosis with Emphasis on Mistaken Diagnosis if Spider Bites," Manuscript in Preparation Abstract.

Vetter, R. (2002) "Myth of the Brown Recluse," http://Spiders.ucr.edu/myth.html.

Vorse et al. (1972) "Disseminated Intravascular Coagulopathy Following Fatal Brown Spider Bite (necrotic arachnidism)," *J. Ped.* 80:1035-1037.

Wasserman et al. (1963) "Loxoscelism and Necrotic Rachnidism," *J. Toxicol. Clin. Toxicol.* 21:451-472.

Wesley et al. (1985) "Dapsone in the Treatment of Presumed Brown Recluse Spider Bite of the Eyelid," *Ophthalmic. Surg.* 16(2):116-117, 120.

Young et al. (2001) "Comparison of Enzymatic Activity from Three Species of Necrotising Arachnids in Australia: *Loxosceles rufescenes, Badumna insignis* and *Lampona cylindrata*," *Toxicon*, 39(12):1941-1943.

Zielinski et al. (2001) "ELISA to Quantify Hexanal-Protein Adducts in a Meat Model System," *J. Ag. Food Chem.* 49(6):3017-3023.

\* cited by examiner

Range of recluse (genus Loxosceles) spiders in the United States

A.

B.

IMMUNOASSAY FOR VENOM DETECTION INCLUDING NONINVASIVE SAMPLE COLLECTION

CROSS-REFERENCE TO RELATED APPLICATION

This application is a divisional of U.S. application Ser. No. 11/550,130 filed Oct. 17, 2006, which claims benefit of U.S. provisional application Ser. No. 60/727,300 filed Oct. 17, 2005, both of which are incorporated by reference to the extent not inconsistent herewith.

ACKNOWLEDGEMENT OF FEDERAL RESEARCH SUPPORT

Portions of this invention were made with funding from the United States Air Force, Surgeon General Office. The United States government has rights in this invention.

BACKGROUND

Envenomations by the brown recluse spider, *Loxosceles reclusa*, are a significant source of morbidity in endemic regions of the United States, and misdiagnoses are common. A survey of physicians in the endemic area has shown the economic viability of an accurate diagnostic test for these spider bites. An optimal *Loxosceles* venom assay entails significant challenges. Unlike the routine construction of enzyme-linked immunosorbent assays (ELISAs) dedicated to the detection of a single protein, this ELISA detects a unique physiologically active protein—sphingomyelinase D (SMD)—abundantly present in a venom containing a myriad of proteins in varying amounts with varying physiological properties. Some of these proteins closely resemble those of other arthropods, making cross-reactivity of proteins a challenge. However, SMD, the major component of venom felt to be responsible for dermal necrosis, has never been reported in any organism other than *Loxosceles* spiders.

*Loxosceles* ("slant-legged") *reclusa* ("shy and retiring") (FIG. 1) and other species belonging to the genus *Loxosceles* are an occasional cause of morbidity and probably a rare cause of mortality in endemic areas (FIG. 2) [Sams01, Cacy99]. Recluse populations become sporadic on either side of the range borders. (From R. Vetter: spiders.ucr.edu with new data in 2002.)

Accurate data on the number of brown recluse envenomations annually is not available. Data collected from poison control centers nationwide show 2,364 brown recluse spider bites (BRSB) reported in 2000, of which 582 had a moderately significant outcome and 21 had a major outcome. [Litovitz01] These data are incomplete and represent a fraction of the total number of probable brown recluse envenomations, which may be estimated by two other methods. Data from our survey of 21 emergency room (ER) physicians and 12 non-ER physicians (FIG. 3) within the central infested area (Missouri, Kansas, Kentucky, Tennessee, Oklahoma, and Arkansas) show an average of 9.62 probable BRSB per year per ER physician. For this emergency room physician population of 3700, a BRSB annual estimate of 35,594 is obtained. For these highly infested areas, emergency room physicians estimate BRSBs comprise 0.4% of the 7.5 million ER visits, or approximately 30,000 probable BRSBs, a similar total. This total includes none of the non-ER visits, which are harder to estimate, and none of the bites out of the central infested area. The total number of possible BRSBs reported by ER physicians is higher, reflected in the total number of test kits needed per year of 17.7 per ER physician or 65,490 tests in the central infested area, an annual market of $1.7 million in central-infested-area ERs alone.

In a review of nineteen documented cases [Sams01a], the most common presenting symptom was pain at the bite site (10 of 19 patients; 53%), which is similar to the frequency of pain in a series including undocumented cases [Cacy99, Gross89]. More common on bites on the extremities, pain begins after two to eight hours and may be severe enough to require narcotics for relief. Pain may be related to sphingomyelinase D degradation of nerve sheath myelin [Clowers96] and may be followed by anesthesia, hypoesthesia, or hyperesthesia [Sams01, Clowers96]. Malaise, fatigue and light-headedness have been reported in multiple cases, with systemic effects more common in children. Anxiety commonly pervades the first days of *Loxosceles* envenomation, with dread of severe necrosis or death and worry about a slowly-healing wound (FIGS. 4 and 5). This is a difficult time for patients and their families, and uncertainty in the diagnosis is an additional burden. The most common of the severe systemic effects is hemolytic anemia, both Coombs-positive and Coombs-negative, which can rarely cause lysis of 70% of the red blood cell mass in hours [ouhsc96]. Rarely, disseminated intravascular coagulation may occur [Shenefelt97, Taylor66]. Eight deaths have been recorded in the medical literature as of early 2001, all lacking an accompanying spider for documentation, with most cases in children, generally following severe hemolysis, renal failure and multisystem failure [Sams01].

Many medical conditions cause necrotic wounds and have been misdiagnosed as necrotic arachnidism, leading to a delay in proper treatment. [Vetter98, Stoecker96, Rosenstein87, Vetter03, Oaven99]. These conditions include: anticoagulant necrosis; arthropod bite, e.g., Biting flies, and assassin bugs, kissing bugs, scorpions [Sams01, Vetter98]; atypical mycobacterial infection [Stoecker96]; Bacterial cellulitis; chemical burns; cutaneous vasculitis [Sams01]; eethyma gangrenosum [Sams01]; factitia; Foreign body [Sams01]; Herpes simplex with immunosuppression; Loxoscelism from other species, such as *L. deserta*, and *L. arizonica, L. rufescens* [Shenefelt97]; lyme disease [Rosenstein87]; lymphomatoid papulosis [Vetter03]; Necrotic arachnidism: other genera such as *egenaria agrestis* (Hobo spider), *Rabidosa* (Lycosa) *antelucana, punctulata* (wolf spider), *Dolomedes scriptus* (fishing spider), *peucetia viridans* (green lynx spider), *Chemacanthium mildei* (sac spider) [Sams01]; necrotizing fasciitis [Maisel94]; pyoderma gangrenosum as seen in FIG. 6 (pyoderma gangrenosum can be distinguished from necrotic arachnidism in cases with multiple inflammatory pustules or dusky, volcano-like hemorrhagic nodules, but a single ulcer can be suggestive of a spider bite and *Loxosceles* envenomations can be followed by pyoderma gangrenosum [Sams01, Hoover90]; syphilitic chancre [Cacy99]; Sweet's syndrome Sams01]; sporotrichosis [Oaven99]; tularemia [Stoecker96]; and ulcers, both diabetic and stasis [Shenefelt97].

Streptococci may be taken as the prototype for a number of bacteria that can cause necrosis. These include *Clostridium difficile, Vibrio vulnificus*, and *Pseudomonas aeruginosa*, (as well as other Gram-negative rods that cause eethyma gangrenosum). Extensive bacterial cellulitis, especially when the lesion is progressing in size and swollen diffusely, needs specific antibiotic and surgical management. In the news in 2002, there was a case of anthrax in a child in New York City, initially misdiagnosed as a spider bite. Cases of tularemia, atypical mycobacterial infections, and even multiple cases of lymphomatoid papulosis [Vetter03] have been initially misdiagnosed as spider bites. Mistaking these lesions for spider bites can have adverse consequences for the patient.

As yet, without clinical tests for loxoscelism, for cases in which the spider has not been recovered, the wound is diagnosed based upon the presence of typical morphology, a compatible history (such as a bite following putting on clothing after long storage), and whether the bite occurred within the expected territorial range. [Sams01] As an example, the wound in FIG. 7, appearing in an email from a physician to one of the inventors, coming from an area of the country with no documented cases of loxoscelism, may well have been due to trauma or abuse rather than to *Loxosceles* envenomation, but we could not be certain. Unfortunately, in this case as in other such cases, the potential for litigation is present, and if this occurs, litigation outcome may depend upon an uncertain diagnosis.

A sensitive and specific clinical test has been sought for envenomations with *Loxosceles reclusa*. A passive hemagglutination inhibition (PHAI) test was reported to be successful in identifying *Loxosceles reclusa* experimental envenomations in guinea pigs, with 90% sensitivity up to three days after venom injection, and 100% specificity as far as false identification of other spider species, but the test is difficult to perform [Sams01, Barrett93]. A lymphocyte transformation test has also been developed, but is rarely used because of expense and delayed appearance of a positive test result [Berger73]. Proteins contained in *Loxosceles* venom are immunogenic with significant titers of anti-*Loxosceles* IgG antibody formation when venom is inoculated multiple times in the rabbit model [Gomez99]. However, antibody response in humans, across *Loxosceles* species, appears to be weak. Only four of 20 patients bitten with *L. gaucho* and treated with serum therapy had antibodies to *L. gaucho* venom [Barbaro92]. In another study, there were no antibodies to *Loxosceles* venom in measurements taken out to 30 days [Guilherme01]. Thus several experimental methods have been developed to detect the presence of *Loxosceles* venom, but none are simple enough to be commercially available for confirmation of envenomation in patients with suspected *Loxosceles*-induced lesions.

Immunoassay methods and devices comprising swabs used for analyzing samples are known to the art. U.S. Patent Publication No. 2005/0136553 discloses a device in which a swab is contacted by a fluid contained in a fluid chamber via a flow channel, and also containing an assay in fluid communication with the swab, the fluid chamber and the flow channel. U.S. Pat. No. 6,248,294 describes a substantially self-contained diagnostic test for collecting and analyzing a biological specimen having a tubular housing defining a specimen chamber for receiving a biological specimen collected from a swab. U.S. Pat. No. 4,582,699 discloses a kit for detection of gonorrhea in which an inert strip with antibody to the antibody to be detected immobilized thereon is inserted into the sample and subsequently exposed to a reagent for detecting binding. U.S. Pat. No. 4,916,057 describes an immunoassay procedure for detection of *Chlamydia trachomatis* antigen in a sample collected on a swab comprising extracting the sample from the swab with a basic solution that is subsequently neutralized before conducting the immunoassay. U.S. Pat. Nos. 5,753,262 and 4,943,522 disclose lateral flow immunoassays used as pregnancy tests. U.S. Pat. No. 5,163,441 describes a swab for collecting microbiological cultures comprising a swabbing tip made with a non-toxic polyurethane foam having open cells at its exposed surface. U.S. Pat. No. 5,084,245 discloses a device and method involving expressing liquid from the swab for analysis.

All patents and publications referred to herein are incorporated by reference to the extent not inconsistent herewith for the purpose of providing written description and enablement of art-known aspects of this invention.

SUMMARY

An optimal *Loxosceles* venom assay entails significant challenges. Unlike the routine construction of ELISAs dedicated to the detection of a single protein, this ELISA detects a unique physiologically active protein—sphingomyelinase D (SMD) abundantly present in a venom containing a myriad of proteins in varying amounts with varying physiological properties. Some of these proteins closely resemble those of other arthropods, making cross-reactivity of proteins a challenge. However, SMD, the major component of venom felt to be responsible for dermal necrosis, has never been reported in any organisms other than in *Loxosceles* spiders. The limits of sensitivity were previously unknown, and our research has allowed an estimate of both the smallest amount of venom detectable as well as the clinical time limits of the assay and preliminary determination of sensitivity and specificity with biological controls. We have also compared polyclonal antibodies raised in sheep and rabbits, both via crude venom inoculations and sphingomyelinase D, highly purified from crude venom via affinity chromatography. We have determined that polyclonal antibodies raised in rabbits allow more sensitivity in the polyclonal ELISA assay than those raised in sheep. Clinical application of an optimized assay saves the morbidity and expense due to inappropriate diagnosis and treatment of various skin conditions with presentations similar to *Loxosceles* envenomations. In addition, techniques used in the successful detection of this spider venom can be broadly applied and enable the production of assays for the detection of other clinical relevant protein markers for other envenomations and other foreign proteins.

This invention provides a method of diagnosing a bite or sting of a venomous organism in a patient having symptoms consistent with such a bite or sting. The patient can be a human or animal such as a mammal. The method comprises collecting a sample comprising venom from said venomous organism from the area of the suspected bite or sting using a swab; contacting the sample with an antibody which specifically binds to an antigenic site on venom present in the sample; and detecting a complex formed by binding of the antibody and the antigenic site. Venom is a poisonous secretion of a venomous organism, such as a snake, spider, scorpion, wasp, bee, or jellyfish, usually transmitted by a bite or sting. The term "diagnosing" as used herein means identification of the venomous organism that produced the injury. To "collect a sample comprising venom" means to obtain a sufficient amount of material from the site of the bite or sting to be able to diagnose the bite or sting. The material containing the venom can be blister fluid or tissue and/or liquid from a lesion or surrounding skin. The "area of the bite" means an area about one cm of a visible wound (over a diameter of 2 cm, with this diameter ranging from about 1-5 cm).

A swab is a piece of absorbent or adsorbent material, which means material capable of taking up material containing venom from the site of a bite or sting. The material can be any such material known to the art, e.g., cloth comprised of natural or synthetic materials, e.g., cotton, bibulous paper, Dacron rayon, or nylon, or fibers made of such materials, e.g., cotton balls, medical gauze, paper, sponge, polymeric foam such as polyurethane foam, brushes with absorbent or adsorbent bristles that allow the collection of cells such as the Cytette nylon brushes of Birchwood Laboratories, Inc., Eden Prairie, Minn. that are useful for rotation within a narrow aperture, or the Panasonic electric shaver cleaning brush available through totalvac.com; and Q-tip™-type devices such as the cotton swabs made by Unilever Company, and the rayon Scopette™ swabs of Birchwood Laboratories, Inc., typically modified to have a larger head. Bristles that are not absorbent or adsorbent taken singly, can be combined into "brushes" that are absorbent or adsorbent and capable of picking up sample material. The absorbent or adsorbent material can be attached to a stick or other handle or can be manipulated by hand without a handle. The swab may be dry, in which case fluid such as saline can be added to carry the antigens on the swab into contact with antibodies in the immunoassay, or the swab may be premoistened with a fluid such as saline as supplied as part of an immunoassay kit, or may be premoistened by the user at the time of taking the sample.

The method of collecting the sample is non-invasive, and does not require cutting or injecting needles into patients who are typically anxious and in pain, and who may be children or elderly people who do not tolerate pain well.

The detecting can be performed by any method known to the art, as more fully described hereinafter, including sandwich immunoassays and electrochemical immunoassays. In addition, other means for determining the presence or absence of a selected venom protein, e.g., performing western blots, tests, protein function tests, and other assays known to the art can be used.

In one embodiment, the detecting is done using an immunoassay device "in the field," i.e., outside a laboratory. Such devices include, for example, cartridge test devices and dipstick test devices. The device comprises at least one first monoclonal and/or polyclonal antibody specific to a venom protein, a support for the first monoclonal or polyclonal antibody, means for contacting the first monoclonal or polyclonal antibody with the sample, and an indicator capable of detecting binding of the first monoclonal or polyclonal antibody with the venom protein. In some embodiments, one or more monoclonal antivenom antibodies are used in addition to polyclonal antibodies. The swab can have the anti-venom antibody or antibodies immobilized thereon, and can thus be an integral part of the immunoassay device. For example it can be a paper strip that is subsequently contacted with a tracer to detect the presence of binding between venom antigens and the antibodies. The swab can comprise a liquid to aid in picking up venom-containing material from the site. In some embodiments, after collecting the venom from the site of the suspected bite or sting, the swab can be wiped over a substrate having immobilized antibody thereon, or exposed to a liquid that carries the venom antigens from the swab to a site where they can be contacted with anti-venom antibodies. Or venom-containing liquid can be squeezed from or otherwise extracted from the swab for contact with anti-venom antibodies. In some embodiments, the swab is disposable.

Typically, the sample is collected by gently wiping or soaking the skin with the swab for about one to about 360 seconds, for example, for about thirty seconds. The swab can be flash-frozen to extend the period between taking the sample and testing longer than the seven days to three weeks possible without freezing.

When cells are included in the sample to be tested, the method and/or device can include a cell-lysing step or means using detergent, puncture or other physical or chemical process known to the art.

In the devices of this invention, any indicator means known to the art to detect antibody/protein binding can be used. The indicator means can include second, labeled, monoclonal or polyclonal antibodies which bind to the selected protein, which preferably bind to a substantially different epitope on the selected protein from that to which the first monoclonal or polyclonal antibodies bind, such that binding of the first monoclonal or polyclonal antibody will not block binding of the second antibody, or vice versa. The indicator means can also include a test window through which labeled antibodies can be viewed. Any label (also referred to herein as marker) known to the art can be used for labeling the second antibody. The second antibody can be monoclonal or polyclonal.

When the sample to be assayed is a liquid or is carried by a liquid, and the immunoassay test device is a lateral flow device comprising inlet means for flowing a liquid sample into contact with the antibodies, the test device can also include a flow control means for assuring that the test is properly operating. Such flow control means can include control antigens bound to a support which capture detection antibodies as a means of confirming proper flow of sample fluid through the test device. Alternatively, the flow control means can include capture antibodies in the control region which capture the detection antibodies, again indicating that proper flow is taking place within the device. In a lateral flow device, in which the sample is placed on an absorbent support comprising the detection antibody, the sample window and absorbent support provide means for contacting the antibodies with the sample.

The assay method can also comprising collecting a control sample from a separate site on the patient's body that has not been exposed to the venom, i.e., shows no sign of having been the site of a venomous sting or bite, and the control can be tested using the same immunoassay methods and devices as the sample from the site of the sting or bite.

Many venomous organisms are known to the art, including spiders such as the brown recluse, black widow, funnel web, funnel red, white tail, red back, mouse spider, house spider, wolf spider, trap-door spider, and tarantulas, as well as scorpions, and venomous snakes, such as the eastern diamondback rattlesnake (*Crotalus adamanteus*), the timber rattlesnake (*Crotalus horridus*), the dusky pigmy rattlesnake (*Sistrurus miliarius barbouri*), the Mojave rattlesnake (*Crotalus scutulatus*), the common adder (*Opera berus*), the fer-de-lance (*Bothrops atrox*), the Florida cottonmouth (*Agkistrodon piscivorus conanti*), the eastern coral snake (*Micrurius fulvius fulvius*), and other venomous snakes known to the art. Venomous organisms also include jellyfish such as the box jellyfish (*Chironex fleckeri*), and the irukandji jellyfish (*Carukia barnesi*); wasps and bees. Venomous spiders of genus *Latrodectus, Tegeneria* (including *Tegeneria agrestis*), *Loxosceles, Atrax* (including *Atrax robustus*), *Phoneutri*, and *hadronyche* (including the species *Hadronyche formidabilis, H. infensa, H. valida, H. versuta, H. modesta, H. meridiana, H. adelaidiensis, H. eyrei, H. flindersi, H. venenata, H. pulvinator* and *H. cerberea*) are included within the venomous organism whose stings or bites can be diagnosed by the methods and devices of this invention. The invention is illustrated with respect to the diagnosis of bites of the brown recluse spider, *Loxosceles Reclusa*. Other spiders within this genus for which the method is applicable include *Loxosceles intermedia, Loxosceles laeta, Loxosceles gaucho*, and *Loxosceles rufescens*.

This invention provides an improved method for detecting venom by means of an ELISA modified to reduce blocking antibodies using nonfat milk solids and alkaline phosphatase markers. A variety of markers may be used including immunogold, alkaline phosphatase, beta-galactosidase, glucose oxidase, peroxidase markers, and any enzyme that produces a colored or fluorescent product, as is known to the art for monitoring immune reactions. This ELISA is extremely sensitive and can detect under 24 picograms, e.g., around 20 picograms, of venom in a sample, even after the sample has been exposed to ambient summertime temperatures, e.g., up to 100° F. or more for up to about three weeks prior to the detecting step. The method can distinguish the organism that caused the bite or sting from other species of venomous organism utilizing antibodies specific to particular venoms, which can be produced by methods known to the art, following the teachings herein, using combinations of venom immunoassays with previously-known clinical identification of symptoms. Methods of raising polyclonal antibodies can be optimized over host species. A comparison of species can allow optimization when the optimal species is unknown, as per the sheep and rabbit results above. A suitable species can be determined for any given venom by comparing known methods, for example the production of polyclonal antibodies to scorpion venom in horses, to another species, for example sheep.

This invention also provides an immunoassay kit comprising an antibody capable of binding to an antigen present in a venom; a swab for collecting a sample comprising venom from the area of a venomous bite or sting on a patient's body; and a tracer for detecting binding between the antibody and the antigen. In some embodiments the antibody is immobilized on a solid substrate, and the solid substrate can be a swab as described above.

DETAILED DESCRIPTION

Figure 1:
FIG. 1 depicts a *Loxosceles reclusa* spider feeding on a grasshopper.
Figure 2:
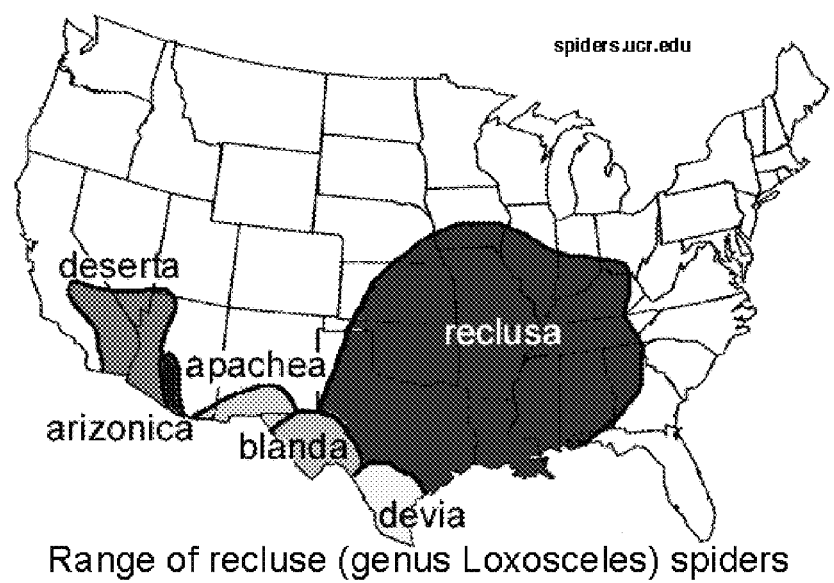
FIG. 2 is a map of the United States showing endemic distributions of the brown recluse (larger area) and five related *Loxosceles* species in the United States, based on Gertsch and Ennik.
Figure 3:
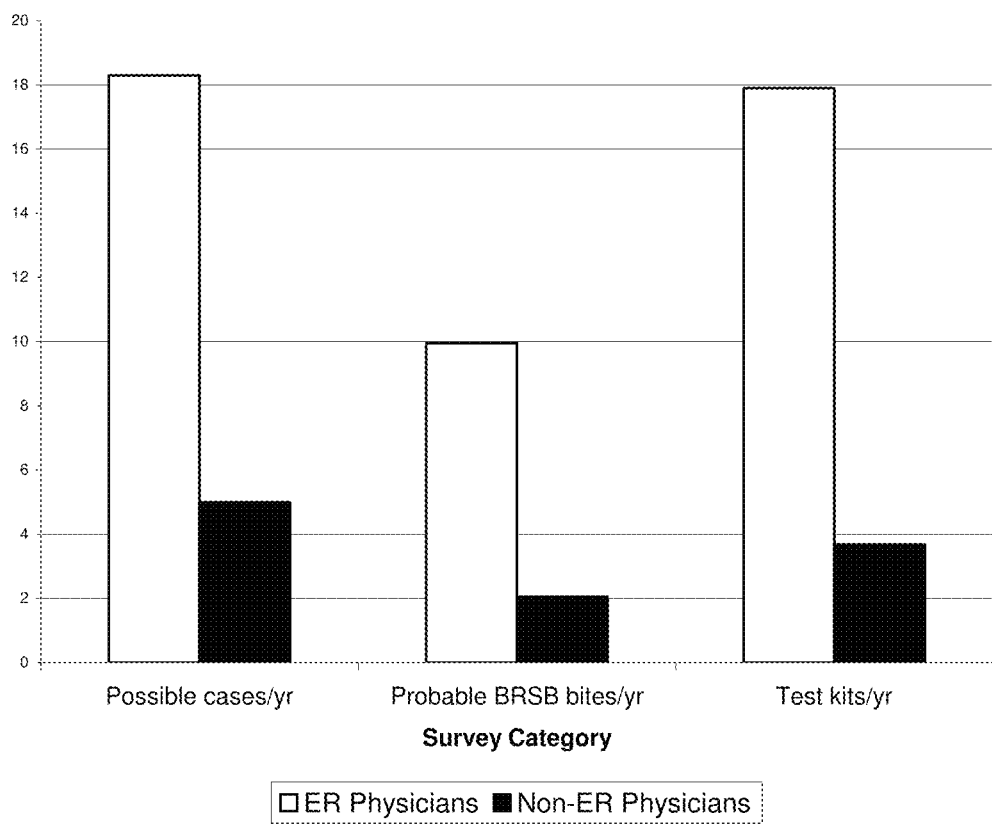
FIG. 3 is a graph showing the results of a telephone and email survey of 33 physicians within the *L. reclusa* area shown in FIG. 2.
Figure 4:
FIG. 4 shows a severe bite of *Loxosceles reclusa*, with a Sams-King certainty of probable on the eighth day.
Figure 5:
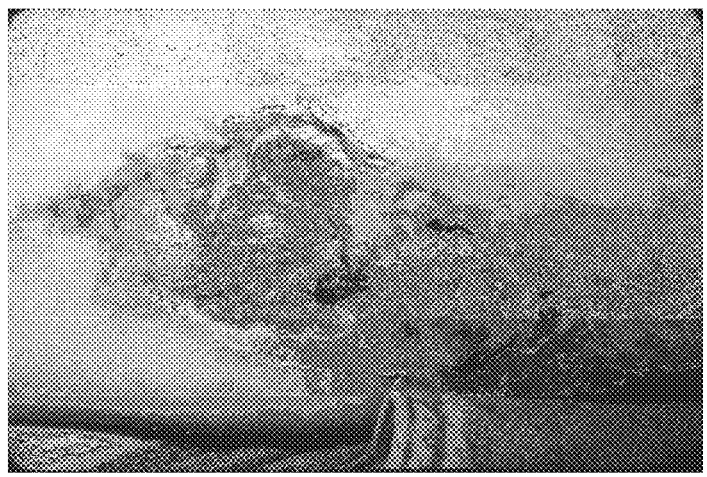
FIG. 5 shows a severe bite of *Loxosceles reclusa*, with a Sams-King certainty of probable, on the 28th day, illustrating the typical slow healing course for large, ulcerated lesions.
Figure 6:
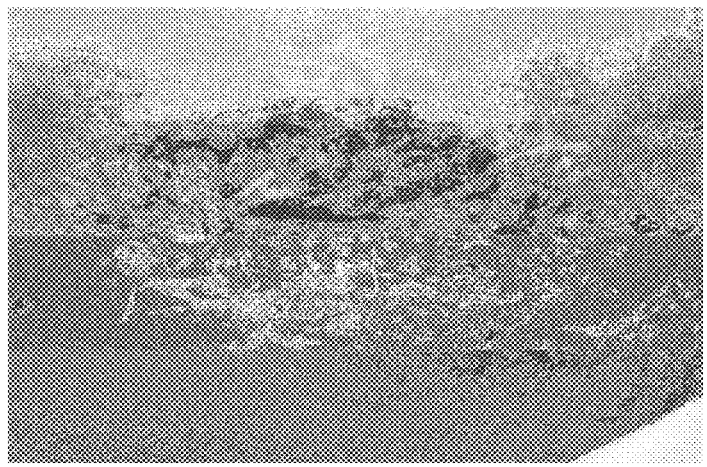
FIG. 6 shows a *Pyoderma gangrenosum* ulcer. Note the typical wet, clean-based ulcer and violaceous overhanging border.
Figure 7:
FIG. 7 shows a necrotic wound with uncertain diagnosis coming from an area in which *Loxosceles recluse* is known to be present.

*Loxosceles reclusa* and related arachnid species are indigenous American spiders that possess a venom capable of causing painful, disfiguring necrotic ulcers with surrounding dermal inflammation and uncommonly, severe systemic effects [Atkins58, Wasserman83, Sams01, Anderson97]. The diagnosis of a brown recluse spider bite is a clinical one made on the basis of the morphologic appearance of the cutaneous lesion [Atkins58, Wasserman83, Sams01, Anderson97]. Definitive diagnosis is problematic because patients generally do not bring the offending spider to the clinician for identification. The appearance of significant envenomation with cutaneous necrosis is the usual basis for diagnosis but is not specific for Loxosceles species envenomation [Sams01, Anderson97, Vetter98], with mimics including a variety of treatable illnesses [Rosenstein87, Rees87, Moaven99]. When significant necrosis is absent, the characteristic features of envenomation are lacking, and the diagnosis is more difficult.

Physicians who practice within the *Loxosceles reclusa* habitat in the central and southern areas of the Midwestern US routinely see patients with suspected spider bites. Unfortunately, we have observed that fewer than 10% of patients bring in the suspect spider for identification. The spider may be found after a significant delay, leading to some uncertainty that the arachnid presented is the offending agent. Therefore, the diagnosis of most spider bites is generally dependent upon analysis of the bite morphology. Severe bites may exhibit the 'red, white and blue' sign described by Sams et al [Sams01] or may show the sunken, bluish patch described by Anderson [Anderson97]. Small bites as described herein lack these features and are not well-characterized. They are likely more frequent in occurrence than the literature suggests. Small bites cannot be diagnosed definitively without the spider or a test that can unequivocally demonstrate the presence of spider venom.

Utilizing the diagnostic tests of this invention, venomous bites can be correctly diagnosed. A sample comprising venom is collected from the area around the bite using a swab, and the material on the swab is immunologically analyzed for the presence of venom.

Various formats may be used to test for the presence or absence of an analyte using the assay. For instance, in certain embodiments, a "sandwich" format is utilized. Examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In addition, other formats, such as "competitive" formats, may also be utilized. In a competitive assay, the labeled probe is generally conjugated with a molecule that is identical to, or an analogue of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambofte, et al.; U.S. Pat. No. 5,670,381 to Jou, et al.; and U.S. Pat. No. 6,194,220 to Malick, et al., which are incorporated herein in their entirety by reference thereto for all purposes.

Any known detection technique may be utilized in the present invention. For example, as is well known in the art, the assay may also be an electrochemical affinity assay, which detects an electrochemical reaction between an analyte (or complex thereof) and a capture ligand on an electrode strip. For example, various electrochemical assays are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

A concern in performing diagnostic assays is to separate immunoreactants that do not bind antigen, and thus do not form part of the immune complex, from bound reactants that form the complex. The presence of unbound reactants can increase the background of the assay. While washing the immune complex can, and, indeed, does remove most of the background signal due to unbound reactants, most assays employ what is termed a blocking step to further reduce the background. The blocking step involves coating the solid support with proteinaceous substances after it has been coated with antibody. The blocking material binds to sites on the solid matrix material which are not covered with antibody, and thus prevents subsequent nonspecific binding of immune reactants that are not part of the immune complex. Generally, the blocking step is performed either before the assay is conducted, hence, necessitating an additional time consuming step, or else, as described in U.S. Pat. No. 3,888,629, the solid matrix material is impregnated with the blocking agent, and then freeze dried and maintained in this state prior to use.

Immunoassay devices suitable for detecting the presence of venom can be in the form of flow-through assay devices, typically contained within a housing, and suitable for collecting samples outside a laboratory. For example, a flow-through immunoassay comprises a porous membrane having a binding reagent immobilized on the membrane. An absorbent material is placed on one side of the membrane. When a sample containing an analyte is applied to the membrane, the sample flows through the membrane by capillary movement. The analyte is then bound to the binding reagent. The assay device may include an absorbent (bibulous) support upon which antivenom antibody is present, and into which sample venom components are absorbed directly upon contact with the swab or by means of a carrier liquid that carries the venom components from the sample on the swab into the absorbent support. The device may also comprise a receiving well for receiving the sample or sample components, preferably having a bibulous material therein to facilitate transfer of the antigens into the well. The receiving well may incorporate the antivenom antibodies.

In one embodiment, the immunoassay test is a colorimetric test that comprises a plastic housing with a well disposed in one end thereof comprising a bibulous material; and a strip of paper in fluid communication with the well extending toward the other end of the housing and having two stripes about 1.5 mm in width running the entire width of the strip, one for control prepainted with venom antigens and antivenom antibodies, as well as markers to indicate binding of the antigens and antibodies, and the other for performing the test prepainted only with antivenom antibodies and markers to indicate binding. When the sample is added to the well by rubbing the swab along with a carrier liquid such as normal saline, the carrier fluid allows binding contact between the prepainted antigens and antibodies on the control stripe and carries venom antigens from the sample into binding contact with the antivenom antibodies on the test stripe. The housing comprises a window or windows positioned above the stripes and is marked to indicate control and test (e.g., C and T). The control stripe always shows the color reaction, but the test does not unless the sample contains venom antigens with which the prepainted antivenom antibodies bind.

A flow-through immunoassay further comprises applying a tracer that is another binding reagent of the analyte with a label for detecting the bound analyte. The binding reagents of the membrane and tracer are selected from a group consisting of antibodies, antigens, receptor proteins, etc. The label can be selected from a group of detectable substances, including enzymes, radioactive isotopes, and particular color particles. The immunoassay can also comprise detector means known to the art for detecting the presence of the label or changes in the label that indicate that binding of a tracer antibody to the detection antibody has occurred. Suitable membranes include glass fiber, polyvinylidene difluoride, polycarbonate, nitrocellulose, nylon, paper, etc., for example as described in U.S. Pat. No. 5,155,022.

As is known in the art, antibodies useful for detecting venom may be polyclonal or monoclonal antibodies, and polyclonal, monoclonal antibodies or both may be used as tracers. Antibodies which bind to venom polypeptides can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, e.g., by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies. See, e.g., Coligan, et al. (current ed.) Current Protocols in Immunology, Wiley Interscience.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The preparation of polyclonal antibodies is well-known to those skilled in the art. See, e.g., Green, et al. "Production of Polyclonal Antisera" pages 1-5 in Manson (ed.) Immunochemical Protocols Humana Press; Harlow and Lane; and Coligan, et al. Current Protocols in Immunology.

The preparation of monoclonal antibodies likewise is conventional. See, e.g., Kohler and Milstein (1975) Nature 256: 495 497; Coligan, et al., sections 2.5.1 2.6.7; and Harlow and Lane Antibodies: A Laboratory Manual, Cold Spring Harbor Press. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al.; Barnes, et al. "Purification of Immunoglobulin G (IgG)" in Methods in Molecular Biology, vol. 10, pages 79 104 (Humana Press, current ed.). Methods of in vitro and in vivo multiplication of monoclonal antibodies are well-known to those skilled in the art. Multiplication in vitro may be carried out in suitable culture media such as Dulbecco's Modified Eagle Medium or RPMI 1640 medium, optionally replenished, e.g., by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Example 1

Venom Fractionation

Commercially available *Loxosceles* sp. spider venoms (SpiderPharm, Yarnell Ariz.) are crude uncharacterized preparations containing multiple polypeptides ranging in size from 10-200 KDa. The purification and biochemical characterization of the active components in these mixtures is fundamental to understanding the potent inflammatory and necrotic effects that these venoms have on skin. We have completed preliminary fractionation of *Loxosceles* sp. venom using anion exchange chromatography. Crude venom was loaded on a HiTrap Q column and eluted with a salt gradient increasing from 20 mM to 1M NaCl in 25 mM TEA buffer pH 7.4. While two earlier studies found three venom fractions in *Loxosceles* sp. using Sephadex G50 and Sephadex G100 column chromatography, the higher resolution of the more sensitive methods used in our studies found two more venom component fractions. Thus, five fractions (to the left of fractions 6-7, FIG. 8) were separated and assayed using the rabbit model of arachnid envenomation. We found using the rabbit dermal model for Loxosceles envenomation that the dermonecrotic activity was found in the first (flow-through) fraction, the leftmost peak.

Figure 9:
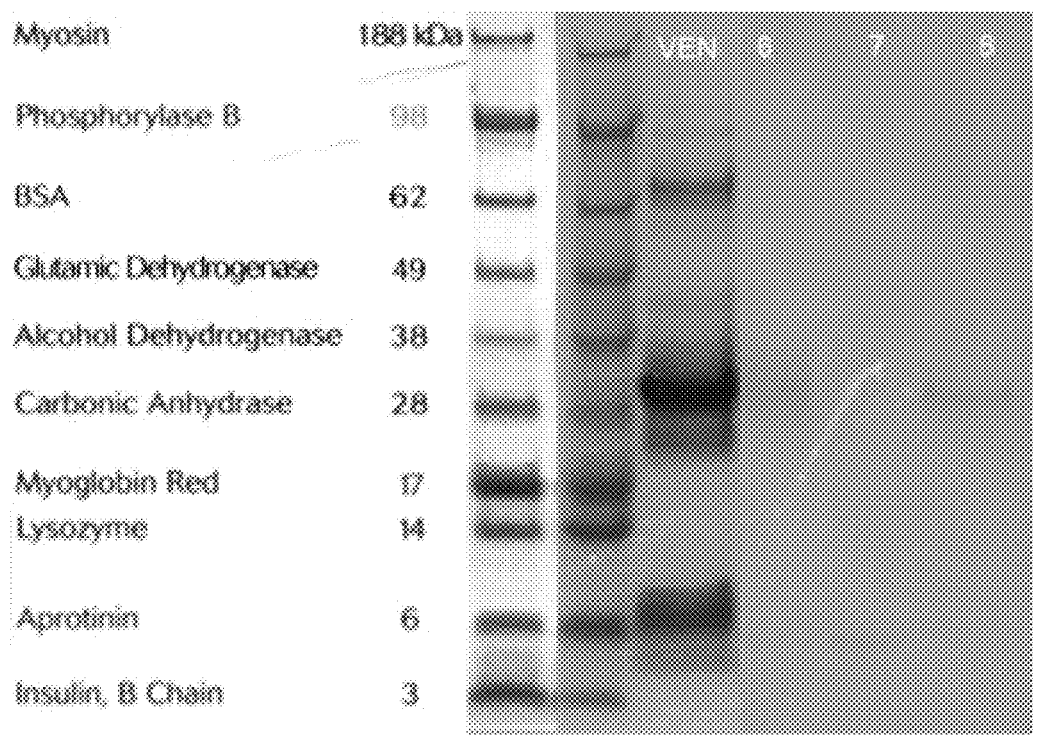
FIG. 9 shows an SDS PAGE (electrophoresis) gel of fractions of crude *Loxosceles* venom (VEN) and analysis of crude venom (see lane marked "VEN"). The multiple protein bands noted in this SDS PAGE demonstrate the multiple proteins contained in venom.

FIG. 9 shows the results of SDS PAGE analysis of crude venom (see lane marked "VEN"). The multiple protein bands noted in this SDS PAGE demonstrates the multiple proteins contained in venom.

Example 2

Characterization of Venom Proteins Via Western Blot

Figure 10:
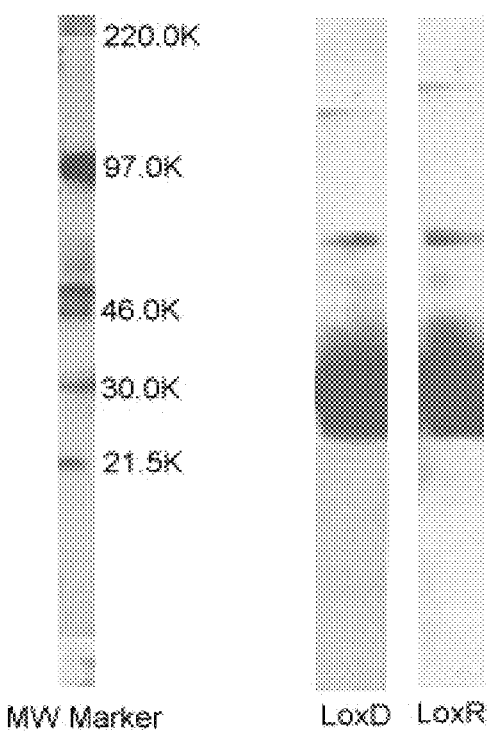
FIG. 10 shows Western blots of *L. deserta* (LoxD) and *L. reclusa* (LoxR) using αLoxRD as the primary antibody. Both venoms revealed prominent signaling in the 30 KDa molecular weight range.

*L. deserta, L. reclusa* venoms and Rainbow™ molecular weight marker (Amersham International, Buckinghamshire, England, RPN 800) were subjected to electrophoresis on 10% sodium dodecyl sulfate (SDS)-polyacrylamide gels and transferred to nitrocellulose [Osborn89]. Blots were analyzed for protein components using αLoxRD (rabbit polyclonal) as the primary antibody at 2 ug/ml. The antibody predominantly recognized a protein(s) migrating close to 28,000$M_r$. See FIG. 10.

Example 3

Serum *Loxosceles* Ag or Ab Detection vs Polyclonal Swab ELISA

Tests were performed to determine whether detection of antibodies in human sera to one or more components of *Loxosceles* venom is an alternate avenue for development of a reliable clinical test, and whether the venom protein can be detected in serum.

Figure 8:
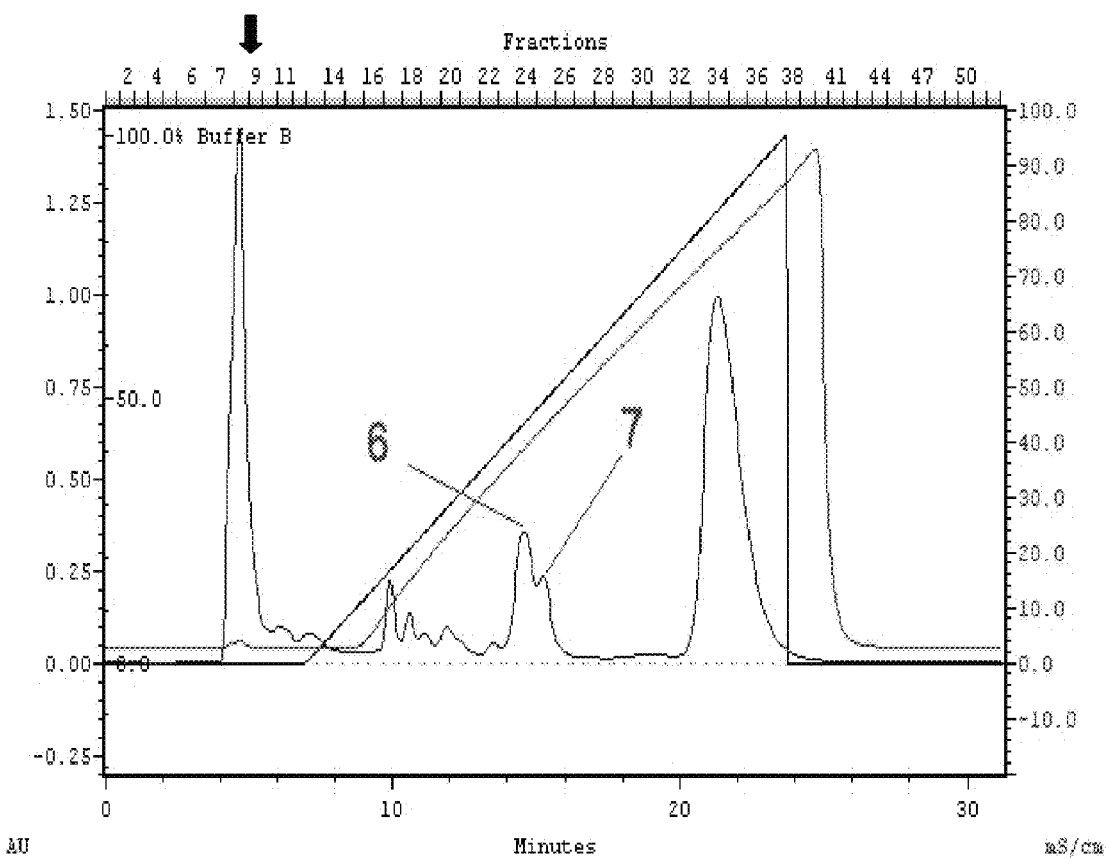
FIG. 8 shows venom fractionation using Sephadex G100 column chromatography. The first peak (arrow) fraction was found to contain dermonecrotic activity. Peaks 6 and 7 may contain the 5 kDa protein shown in FIG. 9.

ELISA titration of human sera from three patients with suspected *Loxosceles* envenomations, with both acute and convalescent sera from patient 3, was performed with whole venom (SpiderPharm, Yarnell Ariz.) and fractionated venom, using the eight protein fractions shown in FIG. 8. All three patients had probable *Loxosceles* envenomations by the criteria of Sams [Sams01]. Wells were coated with 100 ng of buffered crude venom and venom fractions 1-8, and optical densities taken at 30 minutes. Antibodies from patient 1 were obtained 7 days post spider bite, from patient 2-9 and 24 days post spider bite, and from patient 3-150 days post spider bite.

Figure 11:
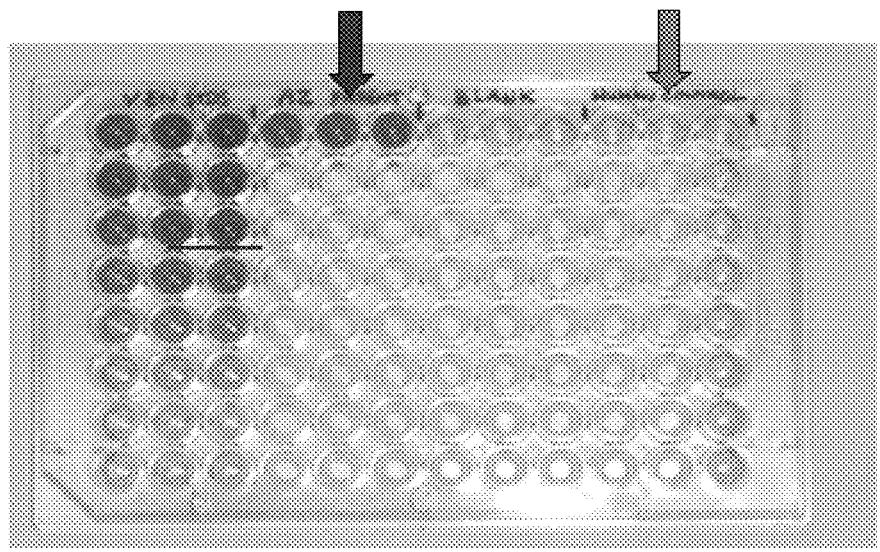
FIG. 11 shows Polyclonal-based ELISA of homogenized dermis from a punch biopsy from an Arizona *L. deserta* victim (see left arrow—positive result is shown in triplicate and underscored.) Compare with the control dermal punch biopsy from a car trauma victim (right arrow).
Figure 12:
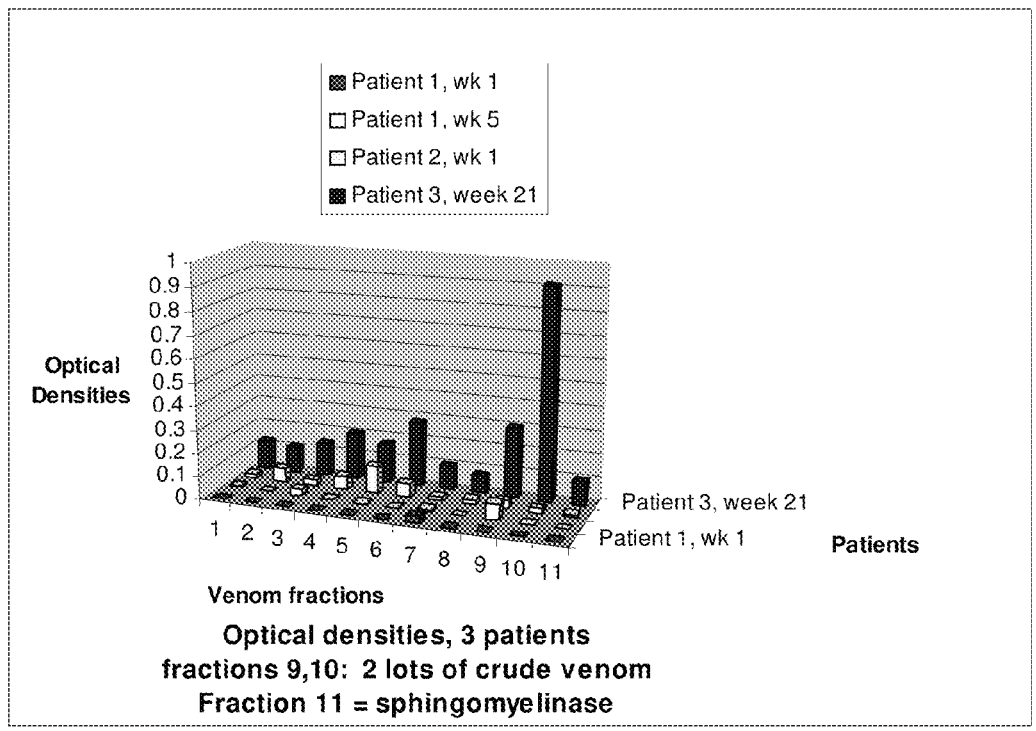
FIG. 12 shows results of standard ELISA at dilutions of 1:100 on sera from patients with probable *Loxosceles* envenomations, against fractions 1-8 of venom and two lots of crude venom and sphingomyelinase, comprising the majority of fraction 1. Preliminary results showed a response by patient 3 at 21 weeks to total venom and other fractions. Note minimal early response and minimal response to sphingomyelinase. Patient 1, week 1=front row; Patient 1, week 5=second row; Patient 2, week 1=third row; Patient 3, week 21=back row.

Readings of the four patient sera were compared with control human sera. A standard ELISA with biotinylated goat antihuman secondary IgG at dilutions of 1:100 was then performed. There was a response by patient 3 at 21 weeks to total venom, with a significant response to fraction 6 and other fractions, as shown in FIG. 11. No significant antibody titers were detected early.

ELISA assays of serum for venom have also been attempted. Four serum samples taken at 6 hours from rabbits and five more from humans at various times, including one documented envenomation, have all shown no venom detected above background levels. Accordingly, acute and convalescent antibody titers and serum venom assays aimed at confirming *Loxosceles* envenomation do not appear to be a viable clinical option, because of an apparently weak antibody response and because of the need for immediate diagnosis. We have accordingly developed antigen-based assays.

Example 4

Polyclonal Assays

The first polyclonal assay had a threshold of detection of approximately 100 pg per well. This was used to detect *Loxosceles* venom in a 4 mm punch biopsy from an Arizona *Loxosceles* spider bite victim [Boyer00]. See FIG. 11. A specimen of *L. arizonica* was discovered in the child's bed. The positive polyclonal assay together and the finding of the spider allowed a definitive diagnosis in a child with significant hemodynamic changes resembling sepsis.

Thereafter, a second polyclonal assay was developed. This was a *Loxosceles* venom competitive polyclonal enzyme immunoassay that was successfully applied to detect *Loxosceles* venom in hair shafts and skin samples obtained from a patient with a probable *Loxosceles* envenomation [Miller00]. Briefly, this patient was bitten by a spider after removing materials purchased from a gun show in a southern region of the U.S. After the patient presented with clinical evidence of a spider bite, we plucked hair from the affected dermal lesion and from a control site in his opposite extremity. Using competitive sandwich polyclonal techniques described in [Miller00], we compared the less invasive hair plucking technique with dermal biopsies obtained from the affected site. Using the competitive enzyme immunoassay technique, the presence of *Loxosceles* venom was detected in the lesional punch skin biopsy tissue (8.2±1.5 ng/ml versus 1.5±0.7 ng/ml in contralateral negative control tissue) and in hairs plucked from the lesion (12.7±3.1 ng/ml versus 1.4±1.6 ng/ml in hairs from the contralateral leg) [Miller00]. This report showed that venom was detected by a relatively non-invasive means (i.e., hair plucking).

Figure 13:
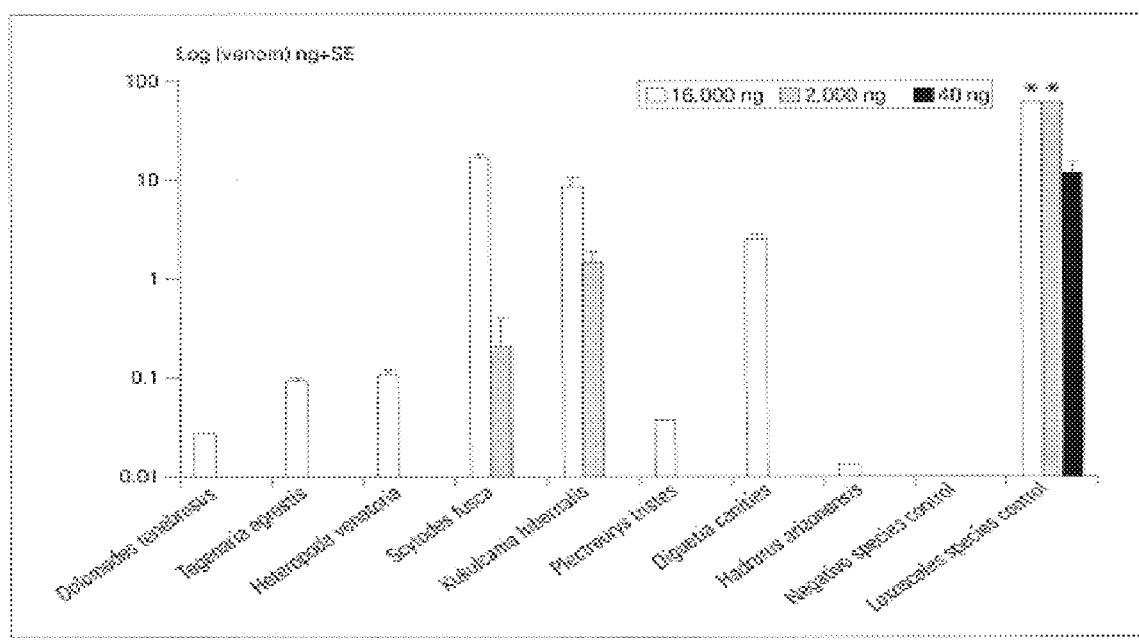
FIG. 13 shows arthropod venoms that cross-reacted to the *Loxosceles* species ELISA at 16,000 ng and 2,000 ng. Only *L. reclusa* control venom reacted with the ELISA at 40 ng. For graphic purposes, the y-axis values are reported as log (data). *Values reported as off the scale by the assay. From [Gomez02].

Our first polyclonal assay could detect *Loxosceles* venom with a threshold of detection of about 100 pg. Seventeen competing venoms (14 arachnids, 2 scorpions, and 1 honeybee venom) required over 2000 ng in the same assay to be detected (FIG. 13). Only *L. reclusa* control venom reacted with the ELISA at 40 ng.

Figure 14:
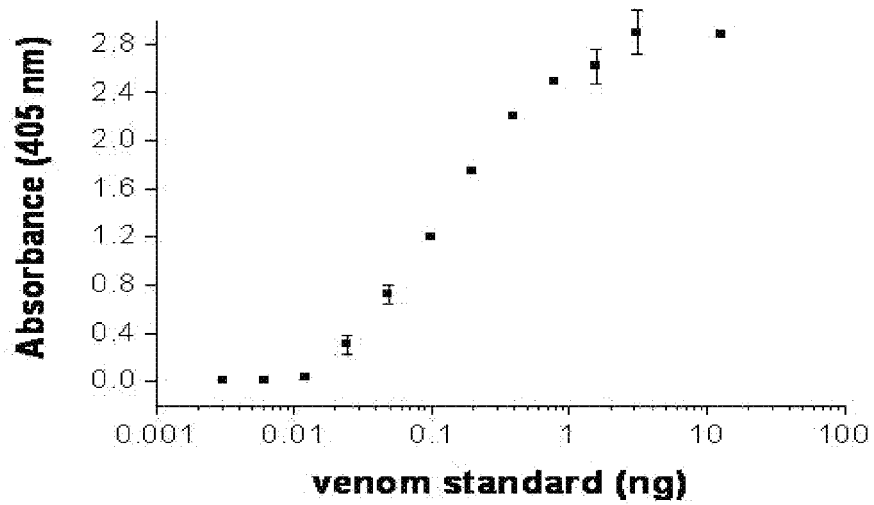
FIG. 14 compares venom standard curves for polyclonal assays using alkaline phosphatase (AP) and horseradish peroxidase (HRP). Detection threshold is 24 pg/well for AP and 49 pg/well for HRP.
Figure 14:
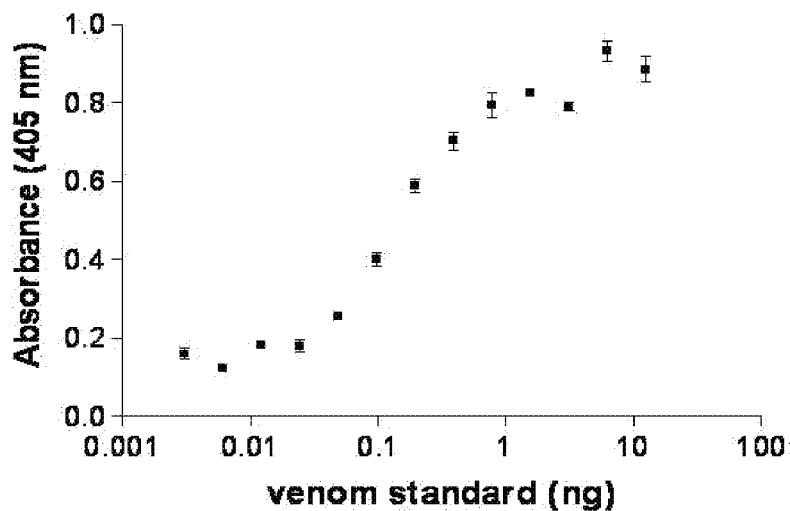
Figure 15:
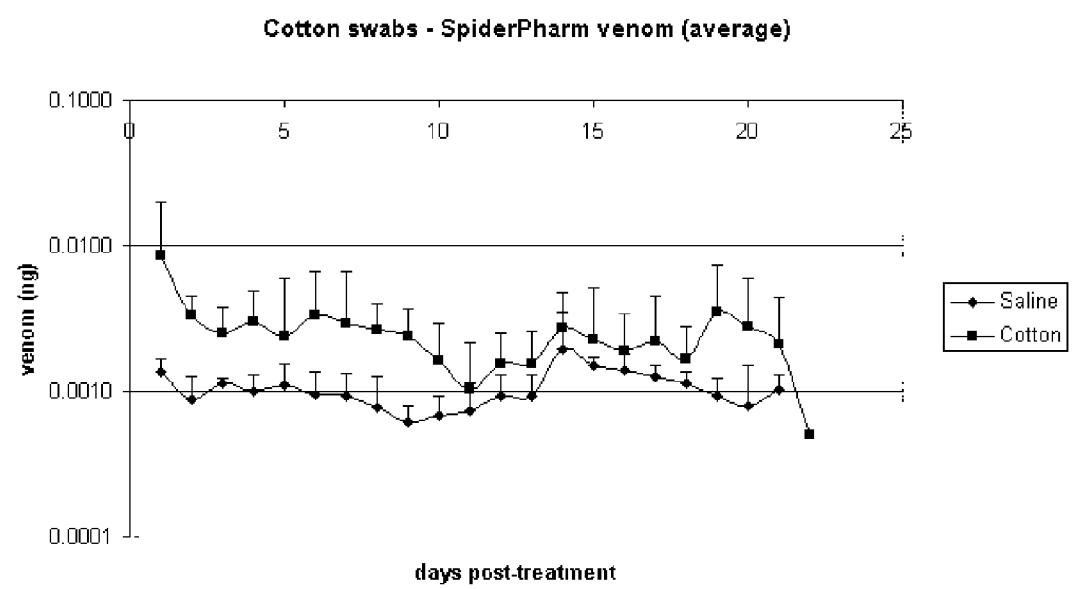
FIG. 15 graphs results of polyclonal assays of injected *L. reclusa* venom, 3-week using whole venom ng, recovered from cotton swabs at the infection site.
Figure 16:
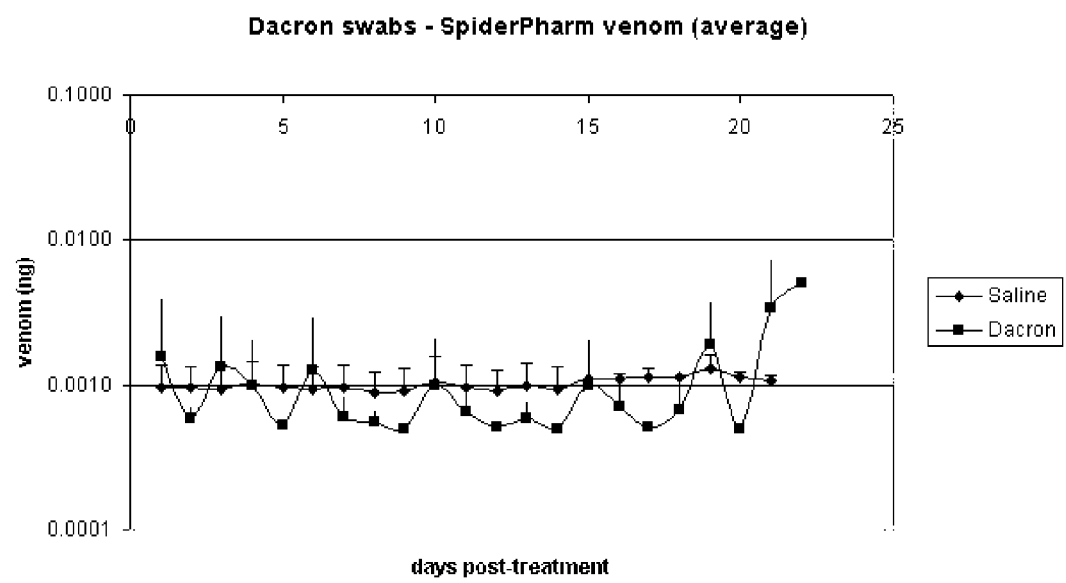
FIG. 16 graphs results (averaged over all rabbits) of polyclonal assays of injected *L. reclusa* venom, 3-week using whole venom ng, recovered from Dacron swabs at the infection site.
Figure 17:
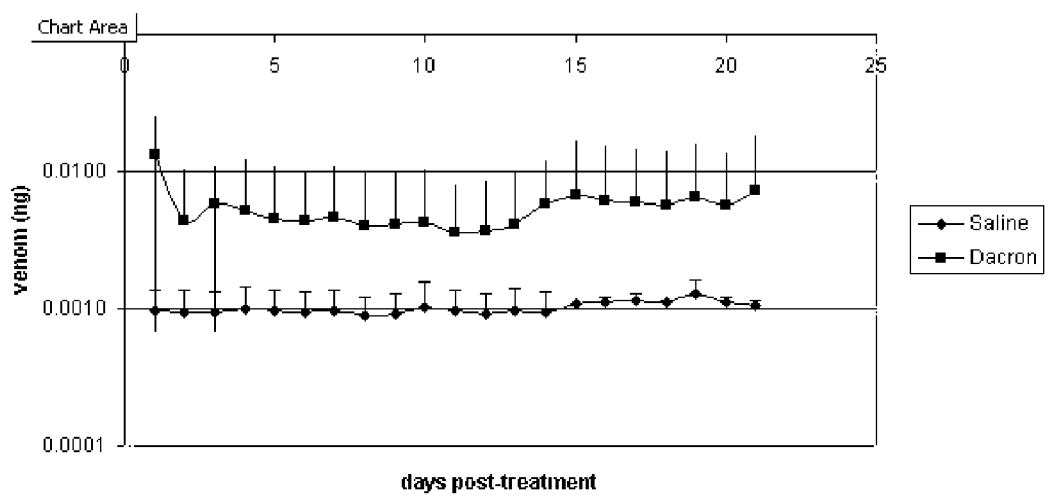
FIG. 17 graphs results of polyclonal assays of injected sphingomyelinase component of *L. reclusa* venom ng, 3-week, recovered from Dacron swabs.
Figure 18:
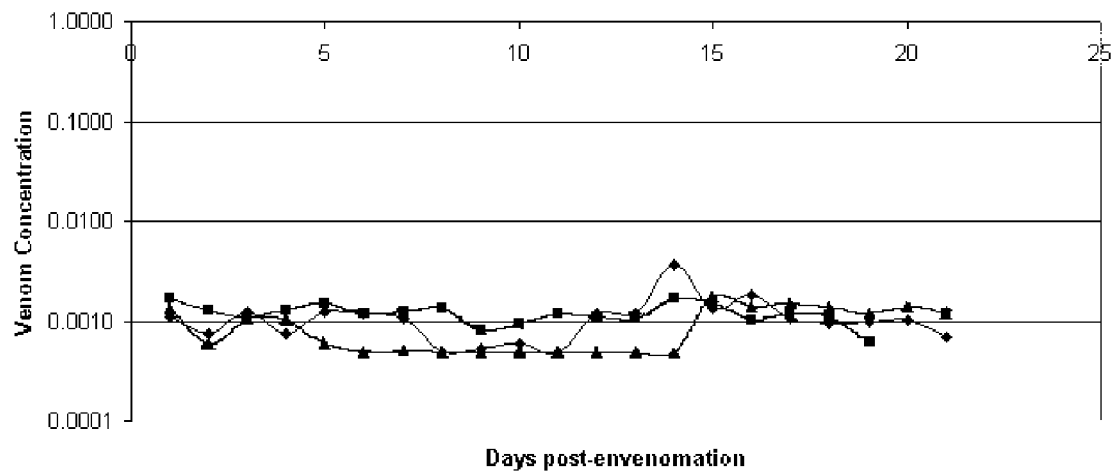
FIG. 18 graphs 3-week ng venom recovered from saline-injected animals, cotton swabs. Each line represents a single rabbit, with a diamond, for example, representing a single rabbit, and a square representing a different rabbit.
Figure 19:
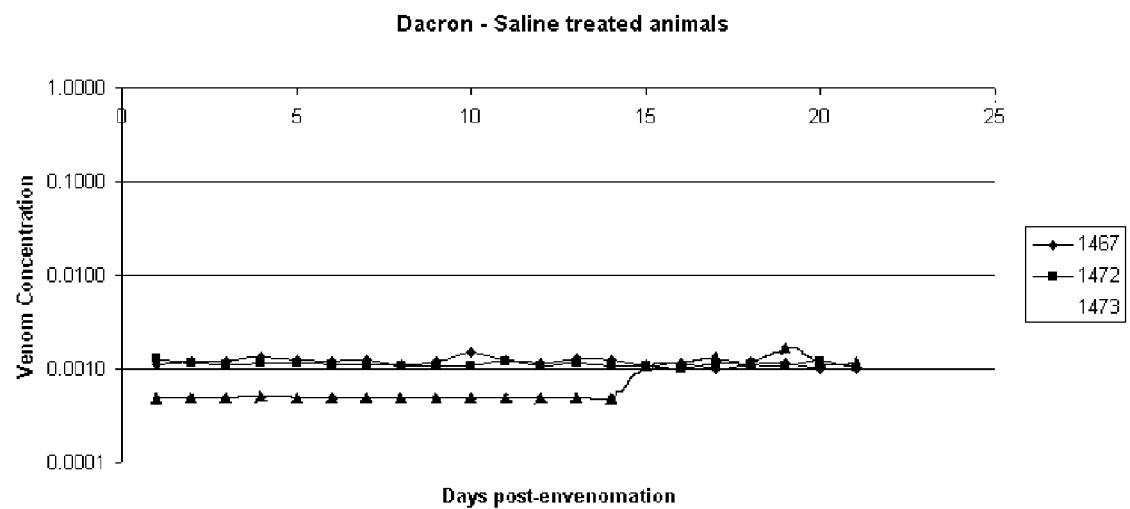
FIG. 19 graphs 3-week ng venom recovered from saline-injected animals, cotton swabs. As in FIG. 18, each line represents a single rabbit, with a diamond, for example, representing a single rabbit, and a square representing a different rabbit.

Several modifications of the first polyclonal assay have allowed a new threshold of detection, 24 pg vs 100 pg previously. The changes include adding nonfat milk solids to the blocking buffer, increasing the concentration of other blocking proteins, allowing the solution to incubate overnight and changing the developing agent to alkaline phosphatase. Venom standard curves are shown for the alkaline phosphatase (AP) assay and horseradish peroxidase (HRP) assay in FIG. 14.

A 24 pg venom well consistently produces an AP signal that is greater than background plus 3 standard deviations. Three necrotic and inflammatory lesions (with no history or examination supporting necrotic arachnidism) had signals at background levels with the second assay.

Example 5

Time Study of Venom Detection in Rabbits Using Cotton and Dacron Swabs

This study was done under amendment #6 to US Military Protocol FWH20020003, "Effects of Venom From the Brown Recluse Spider (*Loxoceles reclusa*) on the Coagulation Mechanism in Rabbits (*Oryctolagus cunniculus*)."

In this amended protocol, FWH20020003A, the 10.0 μg/ml dose of the brown recluse spider venom was found to be a better concentration than a 20.0 μg/ml dose used in previous studies. A dose of 5 μg produces tissue damage that appears to approximate the typical "bite" observed in a brown recluse spider bite. It is probable that the actual bite yields a dose of venom that is quite variable.

This protocol was approved by the Animal Use and Care Administrative Advisory Committee (AUCAC) for the use of eighteen rabbits for the full study. The goal was to find the least amount of venom detected from a swab and the longest period after the bite that it can be detected, i.e., the longest amount of time that the venom is viable in the individual lesions. The number of test subjects was determined for statistical significance. Three animals were saline control subjects. Rabbits were injected in the deep dermis in the middorsal back. The first phase of the study was to obtain data to determine the time course of swab and biopsy venom detection. The biopsied lesions were examined histopathologically to assess the extent and nature of the tissue damage using standard techniques from previous studies.

Biopsy tissues were obtained for "snap freezing" in liquid nitrogen at 24 and 72 hours for venom antigen examination at the University of Missouri. After envenomation and swab and biopsy collections, all animals were euthanized following humane procedures approved by the AUCAC. In the second phase of the study animals are given decreasing amounts of venom (N=2 animals per treatment): 2.5 μg, 1.25 μg, 0.625 μg, 0.3125 ug, 0.1563 μg vs control with saline with daily swabs and biopsies as noted above.

Six adult New Zealand White rabbits were inoculated in the deep dermis with 5 μg of *Loxosceles* venom (SpiderPharm, Yarnell, Ariz.). Four died shortly thereafter with multiple organ failure including pulmonary edema and liver necrosis. Three more were inoculated with 4 μg of *Loxosceles* venom and survived. Saline-injected rabbits were used as controls. Swabs were obtained using the standard 30-second swab method with cotton and Dacron swabs daily for 21 days and biopsy material was obtained in a circular area near the infection site at one, three, seven, and fourteen days.

A similar study was performed in New Zealand White rabbits using the purified sphingomyelinase component of *Loxosceles* venom. Saline injection controls, cotton and Dacron swabs, and the swab technique were the same as in the whole venom experiment above. Results are as shown in FIGS. 15-19, with venom detected as long as three weeks from the 4 and 5 ug doses.

Results show generally that cotton swabs work better than Dacron; venom can be detected out to three weeks and probably more; there is considerable animal to animal variation; the venom fraction that is essentially sphingomyelinase allows detection at least as well as whole venom, although the actual venom protein may be better represented by SpiderPharm (whole) venom; there are oscillations in venom detection day-to-day; there are significant plate-to-plate variations. Standard curves are run for each assay and the venom amounts found on different runs are not strictly comparable, although for all assays run for venom in the rabbit model for cotton, venom amounts are above background for most of the time course studied.

Example 6

Use of Venom Detection Method for Suspected *Loxosceles* Envenomations

Figure 20:
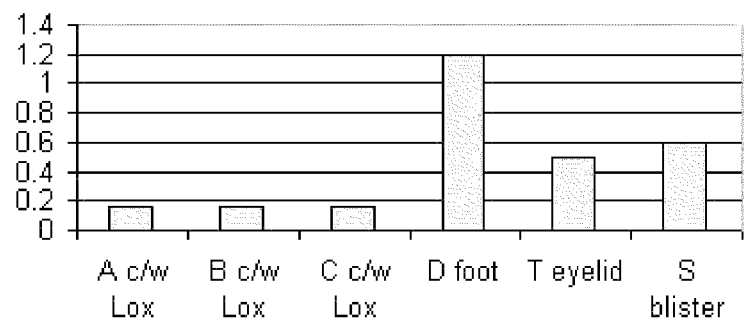
FIG. 20 shows results of assays on six specimens with vertical axis showing pg/well of venom recovered, with raw absorbances corrected for control absorbances. Patients A, B, and C were all judged clinically consistent with *Loxosceles* envenomations, however negative ELISAs provided strong evidence against *Loxosceles* envenomation. Venom concentrations on all three were less than 0.32 pg, shown in the graph as 0.16 pg. Patient D was clinically assessed as a staphylococcal envenomation and culture confirmed MRSA, however the markedly positive ELISA established concomitant loxoscelism. Patient T from Turkey, and patient S from St. Louis were assayed via gauze and blister fluid, respectively, received via express mail. Of the six cases, a brown recluse spider was found only for patient S.
Figure 21:
FIG. 21 depicts the skin appearance of Case B (FIG. 20), showing a bloody blister in a young female, which was rated as a probable *Loxosceles* envenomation but the level of venom antigen via cotton swab was less than 0.32 pg.
Figure 22:
FIG. 22 depicts a painful swollen tender lesion on the foot in a young male (Case D, FIG. 20) with a documented staphylococcal infection at the site with a 5-day history. This was considered to be a staphylococcal infection alone and not a recluse bite until ELISA showed significant venom antigen via cotton swab: 1.2 picogram.

FIG. 20 shows the results of assays on six specimens from suspected *Loxosceles* envenomations. The vertical axis shows pg/well of venom recovered, with raw absorbances corrected for control absorbances. Patients A, B, and C were all judged clinically consistent with *Loxosceles* envenomations, however negative ELISAs provided strong evidence against *Loxosceles* envenomation. Venom concentrations on all three were less than 0.32 pg, shown in the graph as 0.16 pg. Patient D was clinically assessed as a Staphylococcal envenomation and culture confirmed Methicillin Resistant *Staphylococcus Aureus* (MRSA), however the markedly positive ELISA established concomitant loxoscelism. Patient T from Turkey, and patient S from St. Louis were assayed via gauze and blister fluid, respectively, received via express mail. Of the six cases, a brown recluse spider was found only for patient S.

Example 7

Diagnosis of Loxoscelism in a Child Confirmed with an Enzyme-Linked Immunosorbent Assay (ELISA) and Non-Invasive Tissue Sampling A 10-year-old South-Central-Missouri female presented with a two-day history of a painful lesion in the left axilla. The child reported that she noticed the dermal discomfort two days earlier on awakening. During this initial period, the child's mother found a dead spider (later identified) in the girl's bed. On the day prior to presentation, the child developed a headache, severe nausea, and a morbilliform exanthema.

When significant necrosis is absent, as in the case presented here, the characteristic features of envenomation are lacking, and the diagnosis is more difficult. For this case, we utilized a sensitive and ELISA designed to detect *Loxosceles* venom [Gomez02] using a specimen obtained by swabbing the lesion.

Figure 25:
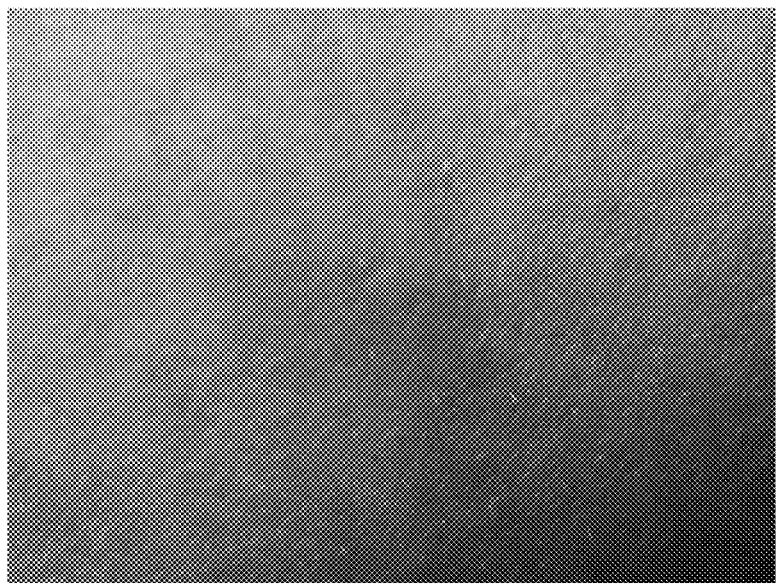
FIG. 25 shows a small painful lesion in 10-year-old Missouri girl caused by a *Loxosceles reclusa* spider bite.

Examination showed a quiet and mildly apprehensive girl with pulse of 96, blood pressure of 98/60 and a temperature of 37.1C (98.7 F). A vesicle on the left axilla was surrounded by a tender, erythematous area with streaks. (FIG. 25). A fine morbilliform exanthem was present on the abdomen and back. The dead spider had been saved by the girl's mother and was later identified by an arachnologist as a member of the species *Loxosceles reclusa* (FIG. 1).

A lesion lacking the usual necrosis or specific signs was confirmed by identification of the *Loxosceles* venom and further confirmed by identification of a spider found in the victim's bed, showing that the sensitive and specific ELISA of this invention, designed to detect *Loxosceles* venom using a specimen obtained by swabbing the lesion, can aid in diagnosis of loxoscelism.

Upon examination the day after original examination, vital signs were unchanged except for the temperature of 36.2° C. (97.2° F.). The exanthem was present as on the previous day. Serum was obtained and a surface swab specimen was obtained non-invasively from the inflamed area in the axilla, using a swab moistened with normal saline, gently rubbing the area for 30 seconds.

The specimens were flash frozen using liquid nitrogen and maintained overnight in a frost-free freezer before moving to a −20 C freezer. The specimens were transported under ice to the University of Missouri-Columbia. The swab was thawed, the absorbent end was removed from the swab stick mixed with 0.05% v/v Tween 20 and was placed in a 1.5 mL microcentrifuge tube and centrifuged at 10,000 g for 10 minutes to remove the saline from the absorbent material. The presence of venom proteins in the solution was detected with an ELISA technique for detecting Loxosceles venom originally described by Gomez et al [Gomez02], with modifications noted herein.

Figure 26:
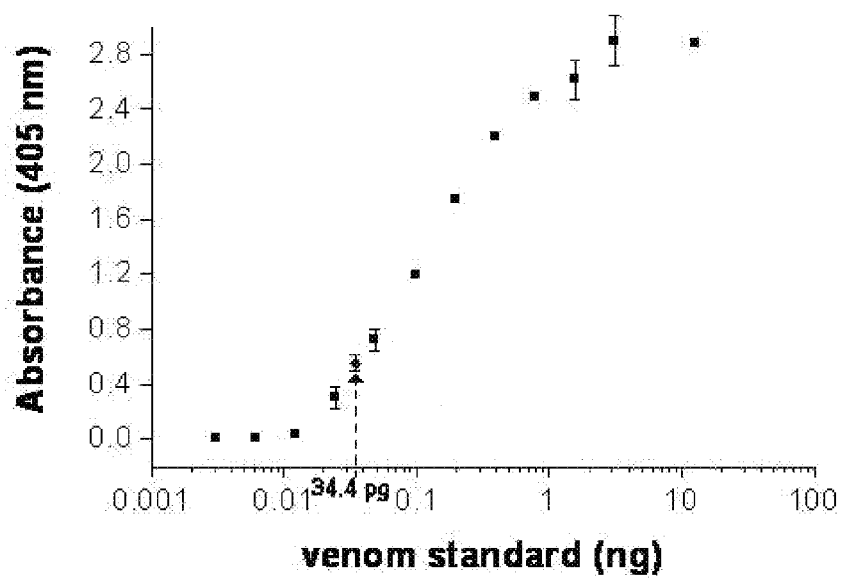
FIG. 26 shows an alkaline phosphatase detection sensitivity curve for venom detection, with venom standards shown as squares and amount detected for the patient depicted in FIG. 25 as a diamond.

Polyclonal capture and detection antibodies were raised in New Zealand white rabbits with unfractionated L. reclusa venom. Antibodies were purified from serum by means of protein A column liquid chromatography [Harlow88]. The concentration of blocking agents as noted in [Gomez01] was increased and nonfat milk solids were added to the blocking buffer. The detection agent was changed from horseradish peroxidase (HRP) to alkaline phosphatase (AP) after standard curves showed greater sensitivity with the AP in the previous assay design. Product generation was monitored at 405 nm on a model ELx808, BIO-TEK, Inc. microplate reader. With the modified methodology, a 24-pg venom standard consistently produced an absorbance that was greater than background plus three standard deviations, with the standard curve as noted in FIG. 26. Necrotic and inflammatory lesions that were tested with the ELISA had absorbances at the background level with this assay. The serum sample collected by phlebotomy also had an absorbance at the background level with this assay. The swab material from this case tested at 34.4±4.3 pg Loxosceles venom protein/well (FIG. 26).

There exists a significant plate-to-plate variation in the ELISA determinations. With some assays, a 0.5 pg venom standard could be distinguished above the background levels.

Features of the case presented here, including nausea, vomiting, headache and an exanthem are seen in a minority of bites. Clinical experience suggests that significant systemic findings are more common in children and can often be associated with small lesions [Wasserman83, Anderson97]. A painful lesion, even when very small, when coupled with these systemic symptoms, can bring the possibility of loxoscelism to the fore in endemic areas when no spider is available for examination. However, for definitive diagnosis in cases where no spider is available, the test by this invention is needed.

The polyclonal swab assay presented here allowed identification of the Loxosceles venom upon the skin three days after the bite. Venom may be detected in patients for an even greater period post spider bite, e.g., up to at least about seven days. Krywko and Gomez reported detection of Loxosceles venom in dermal tissue seven days following envenomation using the rabbit model [Krywko02]. The ELISA assay coupled with a non-invasive means of specimen collection allows confirmation of small, early or atypical presentations of Loxosceles envenomation such as described in this case.

Example 8

Diagnosis of Loxoscelism in Two Turkish Patients Confirmed with an ELISA and Non-Invasive Tissue Sampling Confirmed envenomations due to Loxosceles reclusa have not been previously documented in Turkey, to our knowledge. This example describes two Turkish patients with suspected envenomation by Loxosceles spider bites on the eyelids. Material obtained by swabbing the lesions with gauze was tested using a venom-specific ELISA. Both patients tested positive for the presence of Loxosceles venom.

Loxosceles reclusa and related arachnid species, indigenous to Europe as well as North America possess a venom capable of causing painful, disfiguring necrotic ulcers and, uncommonly, severe systemic effects [Atkins58; Wasserman83; Sams01; Anderson98]. The diagnosis of a brown recluse spider bite is a clinical one made on the basis of the morphologic appearance of the cutaneous lesion [Atkins58; Wasserman83; Sams01; Anderson98]. Definitive diagnosis is usually not possible because patients generally do not bring the offending spider to the clinician for identification. The morphology of a lesion is the usual basis for diagnosis but is not specific for Loxosceles species envenomation [Sams01; Anderson98; Vetter98], as there are many mimics of spider bites [Rosenstein87; Rees87; Moaven99]. For diagnostic confirmation of the two cases presented here, we utilized a sensitive and specific enzyme-linked immunosorbent assay (ELISA) designed to detect Loxosceles venom [Gomez02], using specimens obtained noninvasively by swabbing the lesions with cotton gauze.

Figure 23:
FIG. 23 depicts a tender eyelid lesion in a Turkish patient (Case T, FIG. 20) under the care of an ophthalmologist, presenting with considerable swelling and painful draining eyelid lesion with hemorrhage and massive bilateral eyelid and facial edema. Gauzes were used to wipe the affected and contralateral sites, with shipping to Missouri taking one week. ELISA showed significant venom antigen when compared to control via the gauze method of collection: 0.5 picogram.
Figure 24:
FIG. 24 depicts a hemorrhagic bullae on the arm of a child (Case S, FIG. 20) who was playing in his mother's sewing room, when a toy got stuck behind a stack of boxes, and he stuck his arm behind the stack to retrieve it. His mother recovered the spider, identified as *L. reclusa* by physicians. Significant hematuria and hemolysis marked his hospital course and morphine was needed for pain control. Blister fluid showed significant venom antigen by ELISA: 0.6 picogram.
Figure 27:
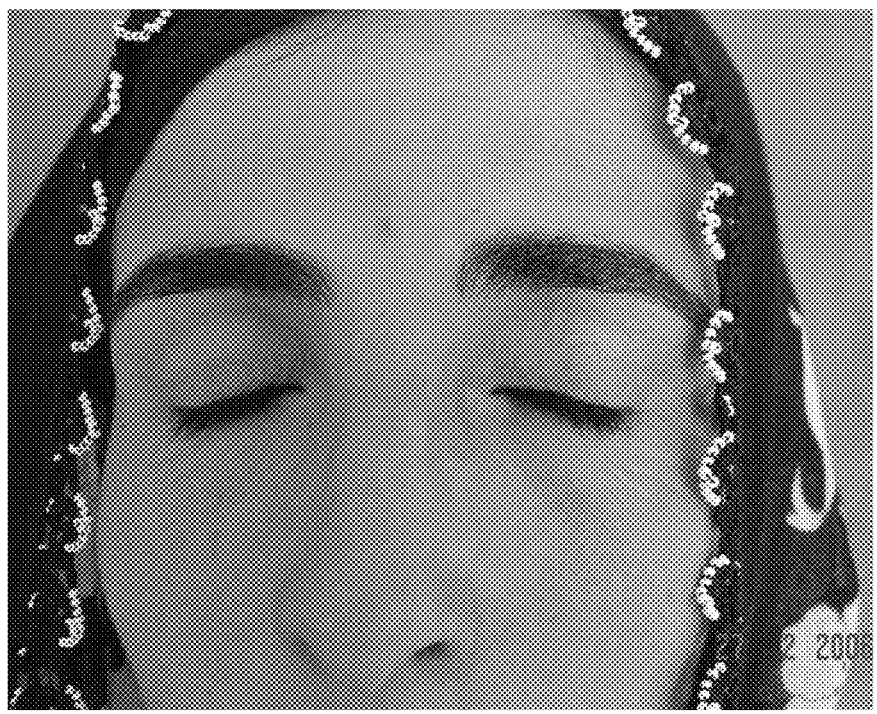
FIG. 27 shows Patient T, Case 1 of Example 8 (see also FIGS. 20 and 23) after healing. No scarring or functional impairments were seen at seven months.

Case 1: A 34-year-old Turkish woman (Case T, Example 6 above) who had gone on a sheep-dealing trip in the rural area of Siirt, Turkey awoke in her tent with swollen, painful pruritic eyelids. She reported that she had seen spiders in her tent but the species was unknown. Within three days, massive facial edema developed, and a 2×3 cm hemorrhagic eyelid lesion with superficial necrosis was present, consistent with loxoscelism (FIG. 23). Upon hospital admission, she had a temperature of 38° C., with a pulse of 80 and blood pressure of 110/70 mm Hg. The results of the laboratory tests, including complete blood count, liver and renal function chemistries, urinalysis and coagulation functions, were all within normal limits. The lesion was managed with saline compresses and ocular lubrication. The lesion healed with resulting normal vision, normal eyelid function and no scarring (FIG. 27).

Figure 28:
FIG. 28 shows Patient Case 2 of Example 8 presenting with a painful eyelid lesion with early necrosis and severe bilateral eyelid and facial edema.
Figure 29:
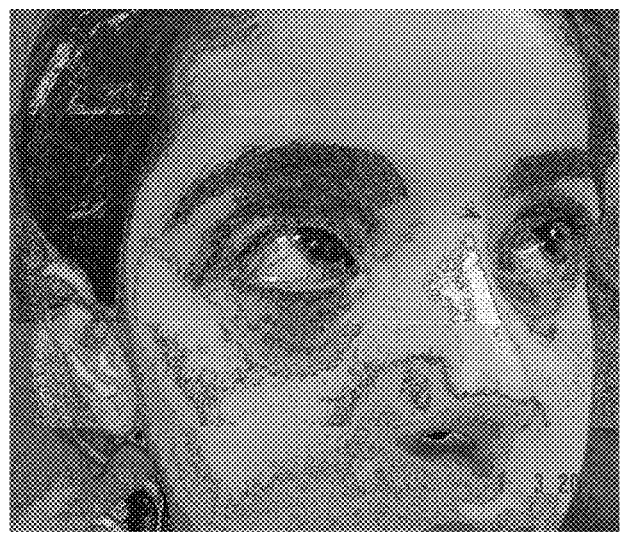
FIG. 29 shows the Patient of FIG. 28 with scarring and hyperpigmentation observed four months after the spider bite.

Case 2: A 7-year-old girl from the rural area of Siirt, Turkey, awoke with pain, pruritus, and mild swelling of the eyelids. Within three days, severe bilateral eyelid edema was present. No spider was identified. On the third day, she was admitted to a hospital. A presumptive diagnosis of brown recluse spider envenomation was made based on the appearance of the lesion. A painful, tender, hemorrhagic lesion showing early necrosis surrounded by severe facial edema was seen (FIG. 28). Upon hospital admission, she was normotensive with a temperature of 38° C., and a pulse of 100. She had a white blood cell count of 17,200/µL with a significant left shift. Hemoglobin and hematocrit levels, urinalysis and other blood indices were within normal limits. The eyelid lesion was managed supportively with saline compresses and ocular lubricants. The lesion healed with scarring and visible hyperpigmentation (FIG. 29). Vision was normal and the eyelid could be opened fully. However, mild epiphora and punctuate epitheliopathy of the affected eyelid were observed. The child's parents observed that the right eyelid was incompletely closed when she slept.

Methods: All specimens for ELISA determination were obtained at the University of Dicle in Turkey. Gauze sponges soaked in normal saline were used to obtain a specimen from the affected lesions and contralateral control sites for both cases. The specimens were collected by gently swabbing the lesion and the control sites for 30 seconds. The swabs were taken on the 7th day after the onset of the lesion in Case 1 and on the 4th day after the onset of the lesion in case 2. Despite shipping by an express carrier, the shipments took 7 and 10 days and were stored in transit in ambient summertime temperatures for unknown durations. After shipment, the cotton samples were moistened with 300 μl of Tris buffered saline containing Tween-20 (20 mM Tris pH8.0; 145 mM NaCl; 0.02% (v/v) Tween-20) and placed in a 0.5 cm diameter plastic centrifuge tube and centrifuged at 10,000 g for 10 minutes to remove the saline from the absorbent material. Venom proteins in the solution were detected using an ELISA technique for detecting *Loxosceles reclusa* venom, originally described by Gomez et al. [Gomez02], with modifications noted herein.

Polyclonal capture and detection antibodies were raised in New Zealand white rabbits with unfractionated *L. reclusa* venom. Antibodies were purified from serum by means of protein A column liquid chromatography [Harlow88]. The concentration of blocking agents as noted in [Gomez02] was increased, nonfat milk solids were added to the blocking buffer, overnight incubation was used, and alkaline phosphatase was used as a detection agent. The generation of paranitrophenol product was monitored at 405 nm on a model ELx808, BIO-TEK, Inc. microplate reader. Separate standard curves were produced for each patient.

Figure 30:
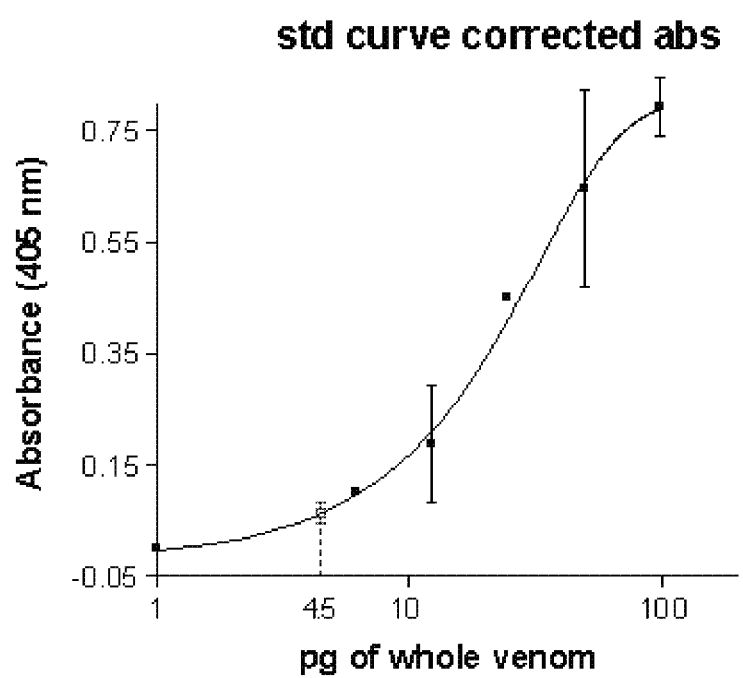
FIG. 30 shows alkaline phosphatase detection standard curves, for Case 1, FIG. 27, showing venom standards as black squares and recovered ELISA venom amount (4.50 pg) at circle.
Figure 31:
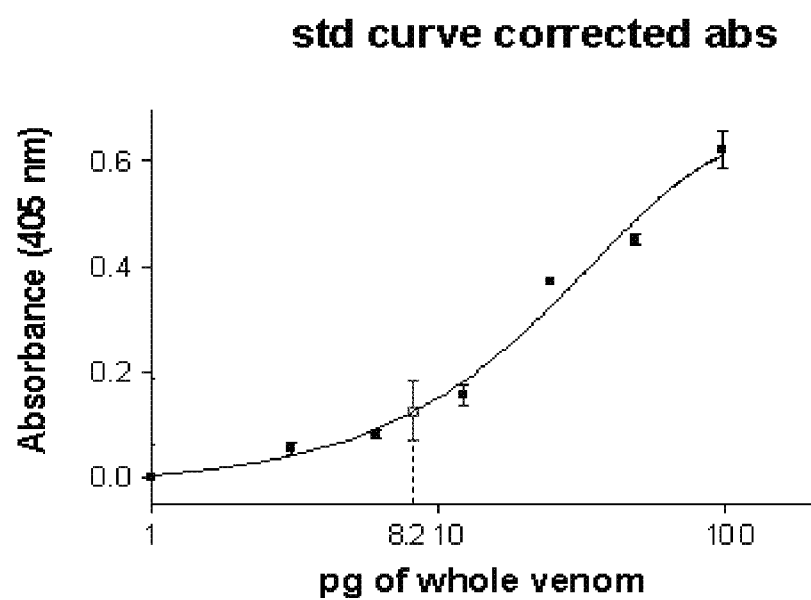
FIG. 31 shows alkaline phosphatase detection standard curve for Case 2, FIG. 28, showing venom standards as black squares and recovered ELISA venom amount (8.2 pg) at circle.

Results and Discussion: The contralateral control specimens all had absorbances at background level. The swab material from both cases showed venom immunoreactivity over three standard deviations greater than background signal, as shown in FIGS. 30 and 31. These results are consistent with the presence of venom from a spider within the *Loxosceles* genus within the samples obtained with gauze from the lesions.

Eyelid brown recluse bites are quite uncommon [Jarvis00; Wesley85; Edwards97]. Severe edema is generally observed. Acute complications include elevated intraocular pressure [12] and airway compromise due to laryngeal swelling [Edwards97]. Long-term complications include necrosis and scarring of the eyelid, which can lead to corneal irritation [Wesley85]. Therapeutic interventions for eyelid brown recluse bites have included dapsone, systemic corticosteroids, hyperbaric oxygen [Jarvis00; Wesley85], and debridement of necrotic tissue with flap reconstruction [Edwards97]. Cantharotomy and cantholysis have been used to restore normal pressure in a case with elevated intraocular pressure [Jarvis00]. Supportive therapy can include topical and systemic antibiotics, saline dressings, and ocular lubricants. A bandage lens has been employed to minimize corneal irritation [Wesley85].

Controlled human trials supporting specific interventions for eyelid brown recluse bites are not available. One study showed benefit from a combination of dapsone and antivenom in experimental eyelid lesions in rabbits [Cole95]. However, another rabbit study reported no benefit from dapsone therapy for clinical outcome in skin lesions induced in rabbits. [Elston05]. Edwards et al. noted that "caution must be emphasized to avoid the overzealous debridement of eyelid tissue. Because of the excellent blood supply, the eyelids [have] a remarkable propensity for self-repair in the setting of gangrenous lid involvement" [Edwards97].

Although lesions attributed to *Loxosceles rufescens* have been reported from Turkey [Atilla04] and nearby areas around the Mediterranean [Borkan95], none of these reported spider bites were confirmed by identification of the spider known to have caused the bite. *Loxosceles rufescens* (Dufour, 1820) is established in Turkey [1.gantep website] and is known to cause necrotic lesions [Young01].

The massive eyelid edema and early necrosis observed in the two cases presented here are consistent with loxoscelism but not diagnostic, as other conditions, particularly envenomations from other arthropods, can have such a presentation. The venom ELISA provided supporting evidence for the diagnosis. Conservative management in the two cases reported here allowed both patients to heal without vision impairment, although one patient had residual functional impairment.

The degree of sensitivity and specificity of the ELISA for *Loxosceles* venom reported here has not been established in clinical cases. In vitro, the ELISA was found to be specific for *Loxosceles* species at relevant antigen levels, reacting to none of 17 other arthropod venoms at 40 ng [Gomez02]. In vivo, necrotic and inflammatory lesions that were tested with the ELISA had absorbances at the background level with this assay. This ELISA is not able to discriminate among *Loxosceles* species, which possess several common protein bands on western blot and display marked antigenic cross-reactivity. [Gomez01]

In summary, the polyclonal swab ELISA assay performed on material obtained by cotton gauze allowed identification of *Loxosceles* venom upon the skin 4-7 days after the onset of symptoms in the two bites reported here, supporting the diagnosis of *Loxosceles* envenomation by a spider of the *Loxosceles* genus in two Turkish patients.

A sensitive and specific *Loxosceles* species venom assay has been provided. In addition to the utility of rapid clinical confirmation of loxoscelism in endemic areas, a venom-based ELISA is useful in exclusion of loxoscelism in the setting of unrelated and treatable illness in nonendemic areas, in defining questionable lesions, and in guiding development of appropriate clinical treatment.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

REFERENCES 1.gantep website 2006. www1 followed by .gantep.edu.tr/ and ~varol/eng/poisonous, accessed Feb. 26, 2006.

Atilla04 Atilla R, Cevik A A, Atilla O D, Yanturali S. Clinical course of a loxosceles spider bite in Turkey. Vet Hum Toxicol. 2004 December; 46(6):306-8.

Atkins58 Atkins J A, Wingo C W, Sodeman W A, Flynn J E. Necrotic arachnidism. Am J Trop Med Hyg. 1958; 7:165-184.

Anderson97 Anderson, P C. Spider bites in the United States. Dermatol. Clin. 1997; 15(2):307-311.

Asbell95 Asbell, P A, Torres M A, Kamenar T et al. Rapid diagnosis of ocular herpes simplex infections. Br J Ophthalm 1995; 79(5): 473-5.

Babcock81 Babcock J L, Civello D J, Geren C R: Purification and characterization of a toxin from brown recluse spider (*Loxosceles reclusa*) venom gland extracts. Toxicon. 1981; 19(5):677-89

Barbaro92 Barbaro K C, Cardoso J L, Eickstedt V R, et al. IgG antibodies to *Loxosceles* sp. spider venom in human envenoming. Toxicon 1992; 30:2227-21.

Barrett93 Barrett S M, Romine-Jenkins M, Blick K E. Passive hemagglutination inhibition test for diagnosis of brown recluse spider bite envenomation. *Clinical Chemistry.* 1993; 39:2104-2107.

Berger73 Berger R S. Millikan L E. Conway F. An in vitro test for *Loxosceles reclusa* spider bites. *Toxicon.* 1973; 11:465-70.

Borkan95 Borkan J, Gross E, Lubin Y, Oryan I. An outbreak of venomous spider bites in a citrus grove. Am J Trop Med Hyg. 1995; 52(3):228-30.

Boyer00 Boyer L V, Theodorou A A, Gomez H F, Binford G J: Spider on the headboard, child in the unit: severe *Loxosceles arizonica* envenomation confirmed by delayed spider identification and tissue antigen detection [abstract]. *J Tox Clin Tox* 2000; 38:510.

Cacy99 Cacy J, Mold J W: The clinical characteristics of brown recluse spider bites treated by family physicians: An OKPRN study. *J Fam Prac* 1999; 48:536-542.

Chavez98 Chavez-Olortegui C, Zanetti V C, Ferreira A P et al. ELISA for the detection of venom antigens in experimental and clinical envenoming by *Loxosceles* intermedia spiders. Toxicon 1998: 36(4):563-9.

Clowers96 Clowers T D. Wound assessment of the *Loxosceles reclusa* spider bite. J Emer Nursing 1996; 22(4):283-287.

Cole95 Cole H P 3rd, Wesley R E, King L E Jr. Brown recluse spider envenomation of the eyelid: an animal model. Ophthal Plast Reconstr Surg. 1995; 11 (3):153-64.

Edwards80 Edwards J J, Anderson R L, Wood J R. Loxoscelism of the eyelids.
Arch Opthalmol. 1980 November; 98(11):1997-2000.

Elston05 Elston D M, Miller S D, Young R J 3rd, Eggers J, McGlasson D, Schmidt W H, Bush A. Comparison of colchicine, dapsone, triamcinolone, and diphenhydramine therapy for the treatment of brown recluse spider envenomation: a double-blind, controlled study in a rabbit model. Arch Dermatol. 2005 May; 141(5):595-7.

Estivill-Torrus98 Estivill-Torrus G, Cifuentes M, Grondona J M et al: Quantification of the secretory glycoproteins of the subcommissural organ by a sensitive sandwich ELISA with a polyclonal antibody and a set of monoclonal antibodies against the bovine Reissner's fiber. Cell & Tiss Res 1998: 294(3): 407-13.

Favre89 Favre C, Wijdenes C, Cabrillat H et al. Epitope maping of recombinant human gamma interferon using monoclonal antibodies. Molecular immunology 26(1): 17-25, 1989.

fda03 FDA Device Advice website: www.fda.gov/cdrh/devadvice/ide/index.shtml

Finke74 Finke J H, Campbell B J, Barrett J T. Serodiagnostic test for *Loxosceles reclusa* bites. *Clin Toxicol.* 1974; 7:375-382.

Gomez99 Gomez H F, Miller M U, Trachy J W, et al. Inhibition of Dermonecrotic Arachnidism with intradermatl polyclonal anti-Loxosceles spider venom Fab fragments. *Academic Emergency Medicine* 1999; 6:1195-1202.

Gomez01 Gomez H F, Miller M J, Waggener M W, Lankford H A, Warren J S. Antigenic cross-reactivity of venoms from medically important North American *Loxosceles* spider species. *Toxicon.* 2001; 39(6):817-24.

Gomez02 H. F. Gomez, D. M. Krywko, and W. V. Stoecker, "A New Assay for the detection of *Loxoceles* (Brown Recluse) spider venom," Ann Emerg Med. 2002 May; 39(5):469-74.

Gross89 Gross A S, Wilson D C, King L E. Persistent segmental cutaneous anesthesia after a brown recluse spider bite. *South Med J* 1989; 83:1321-1323.

Guilherme01 Guilherme P, Fernandes I, Barbaro K C: Neutralization of dermonecrotic and lethal activities and differences among 32-35 kDa toxins of medically important *Loxosceles* spider venoms in Brazil revealed by monoclonal antibodies. Toxicon 2001: 39(9): 1333-42.

Harlow88 Harlow E, Lane D. Antibodies: A laboratory manual. 1988; Cold Spring Harbor Laboratory.

Hoover90 Hoover E L, Williams W, Koger L, et al. Pseudoepitheliomatous hyperplasia and pyoderma gangrenosum after a brown recluse spider bite. [Review] *S Med J.* 1990; 83:243-24.

Huang01 Huang L W, Liu H S, Chang K L: Development of a sandwich ELISA test for arginase measurement based on monoclonal antibodies. Hybridoma 2001: 20(1): 53-7.

Jarvis00 Jarvis R M, Neufeld M V, Westfall C T. Brown recluse spider bite to the eyelid.
Opthalmology. 2000 August; 107(8):1492-6.

Kalapothakis02 Kalapothakis E, Costa Araujo S, de Castro C S et al: Molecular cloning, expression and immunologic properties of LiD1, a protein from the dermonecrotic family of *Loxosceles* intermedia spider venom. Toxicon 2002; 40:1691-99.

King92 King L A, and R D Possee. The Baculovirus Expression System: A laboratory manual. Chapman and Hall, UK. 1992.

Krywko02 Krywko D M, Gomez H F: Detection of *Loxoseles* species venom in dermal lesions: a comparison of 4 venom recovery methods. Ann Emerg Med 2002; 39(5):475-80.

Litovitz01 Litovitz T L, Klein-Schwartz W, White S et al: 2000 Annual report of the American Association of Poison Control Centers Toxic Exposure Surveillance System. Am J Em Med 19(5): 337-395, 2001.

Lopez-Ferber95 Lopez-Ferber M, Sisk W P, Possee R D. Baculovirus transfer vectors. Methods Mol Biol 1995; 39: 25-63.

Maclean03 MacLean J A, Green J A, Roberts R M: Atypical Kunitz-type serine proteinase inhibitors produced by the ruminant placenta.

Maclean03 MacLean J A, Roberts R M, Green J A: Atypical Kunitz-type proteinase inhibitors produced by the ruminant placenta. *Biol Reprod.* 71:455-463; and Maclean J A, Chakraborty A, Xie S, Bixby J A, Roberts R M, Green J A (2003). A family of Kunitz proteins from trophoblast: Expression of the trophoblast Kunitz domain proteins (TKDP) in cattle and sheep. Mol Reprod Devel. 65:30-40.

Maisel94 Maisel R H, Karlen R. Cervical necrotizing fasciitis. *Laryngoscope.* 1994; 104(7): 795-798.

McGlasson93 McGlasson D L, Babcock J L, Berg L, Triplett D A: ARACHnase. An evaluation of a positive control for platelet neutralization procedure testing with seven commercial activated partial thromboplastin time reagents. *Am J Clin Pathol.* 1993 November; 100(5):576-8. Erratum in: Am J Clin Pathol 1994 February; 101(2):

Miller00 Miller M J, Gomez H F, Snider R J et al. Detection of *Loxosceles* venom in lesional hair shafts and skin: application of a specific immunoassay to identify dermonecrotic arachnidism. *Am J Emerg Med.* 2000; 18:626-628.

Moaven99 Moaven L D, Altman S A, Newnham A R. *Sporotrichosis* mimicking necrotising arachnidism. *Med J. Aust.* 1999; 171:865-868.

Munro97 Munro C J, Laughlin L S, Illera J C et al. ELISA for the measurement of serum and urinary concentration of chorionic gonadotropin in the laboratory macaque. Am J Primatol 1997: 41(4): 307-22.

Oaven99 Oaven L D, Altman S A, Newnham A R. *Sporotrichosis mimicking necrotising arachnidism.* [letter]. Med J Aust 171: 685-686, 1999.

Osborn89 Osborn, K., Kunkel, S, and Nabel, G. J., 1989. Tumor necrosis factor and interleukin 1 stimulate the human immunodeficiency virus enhancer by activation of nuclear kB. Proc. Natl. Acad. Sci USA, 86 ( ), 2336-2340.

ouhsc96 Website fammed.ouhsc. December 96.

Pedrosa02 Pedrosa M F F, de Azevedo I L M J, Goncalves-de-Andrade R M et al: Molecular cloning and expression of a functional dermonecrotic and haemolytic factor from *Loxosceles laeta* venom. Biochem Biophys Res Communications 2002; 298:638-645.

Racchetti87 Racchetti G, Fossati G, Comitti R et al: Production of monoclonal antibodies to calcitonin and development of a two-site enzyme immunoassay. Mol Immunol. 1987 November; 24 (11):1169-76.

Rees87 Rees R, Campbell D, Rieger E, King L E. The diagnosis and treatment of brown recluse spider bites. *Ann Emerg Med.* 1987; 16:945-949.

Rosenstein87 Rosenstein E D, Kramer N. *Lyme disease misdiagnosed as a brown recluse spider bite* [letter]. Ann Intern Med 107: 782, 1987.

Sams01 Sams H H, Dunnick C A, Smith M L, et al: Necrotic arachnidism. *J Am Acad Dermatol* 2001; 44:561-573.

Sams01a Sams H H, Hearth S B, Long L L, et al. Nineteen documented cases of *Loxosceles reclusa* envenomation. *J Am Acad Dermatol* 2001; 44:603-608.

Shenefelt97 Shenefelt P D. Brown recluse and other North American spider bites, Chapter 18-25, in Demis D J ed: *Clinical Dermatology*, ed CD-98. Philadelphia, Lippincott-Raven, 1997:1-13

Smith85 Smith P K, Krohn R I, Hermanson G T et al: Measurement of protein using bicinchoninic acid [published erratum appears in Anal Biochem 1987; May 15, 163(1): 279], Anal Biochem 1985; (150)76-85.

Smith88 Smith D B, Johnson K S: Single-step purification of polypeptides expressed in *Escherichia coli* as fusions with glutathione S-transferase, Gene 67 (1988) 31-40.

Stoecker96 Stoecker W V. *Update on computer applications in dermatology*, Missouri Derm. Soc., Kansas City Mo., October 1996.

Tajima98 Tajima T, Yoshizaki S, Nakata E et al. Production of a monoclonal antibody reacted broadly with feline calicivirus field isolates. J Vet Med Sci 1998: 60(2): 155-60.

Taylor66 Taylor E H, Denny W F. Hemolysis, renal failure and death, presumed secondary to bite of brown recluse spider. *S Med J* 1966; 58: 1209-1211.

Vetter98 Vetter R S, Visscher P K. *Bites and stings of medically important venomous arthropods*. Int J Dermatol 37: 481-496, 1998.

Vetter03 Vetter R, Thomason and Bush S. Misdiagnosis of lymphomatoid papulosis as a spider bite. Manuscript in preparation Vorse72 Vorse H, Seccareccio P, Woodruff K, Humphrey G B. Disseminated intravascular coagulopathy following fatal brown spider bite (necrotic arachnidism). *J Pediatr* 1972; 80:1035-1037.

Wasserman83 Wasserman G S, Anderson P C, Loxoscelism and necrotic rachnidism. *J Toxicol Clin Toxicol.* 1983-1984; 21:451-472.

Wesley85 Wesley R E, Ballinger W H, Close L W, Lay A M. Dapsone in the treatment of presumed brown recluse spider bite of the eyelid. Ophthalmic Surg. 1985; 16(2):116-7, 120.

Young 01 Young A R, Pincus S J. Comparison of enzymatic activity from three species of necrotising arachnids in Australia: *Loxosceles rufescens, Badumna insignis* and *Lampona cylindrata*. Toxicon. 2001; 39(12):1941-3.

Zielinski01 Zielinski T L, Smith S A, Pestka J J et al: Elisa to quantify hexanal-protein adducts in a meat model system. J Ag Food Chem 2001: 49(6): 3017-23.

The invention claimed is:

1. A method of diagnosing a *Loxosceles* spider bite in a patient, said method comprising: (a) collecting a sample comprising venom from the area of the bite using a swab; (b) contacting the sample with an antibody which specifically binds to *Loxosceles* venom present in the sample; and (c) detecting a complex formed by binding of said antibody to said venom with a tracer.

2. The method of claim 1 wherein said swab comprises an absorbent or adsorbent material selected from the group consisting of cotton, synthetic fibers, rayon, polyurethane foam, brushes, paper and sponge.

3. The method of claim 1 wherein said detecting is performed by a method selected from the group consisting of: sandwich immunoassays and electrochemical immunoassays.

4. The method of claim 1 wherein said detecting is performed using an immunoassay device outside a laboratory.

5. The method of claim 1 wherein said swab also comprises said antibody.

6. The method of claim 1 wherein said swab is disposable.

7. The method of claim 1 wherein said sample is collected by gently wiping or soaking the skin with said swab for about one to about 360 seconds.

8. The method of claim 1 also comprising collecting a control sample from a separate site on the patient's body that has not been exposed to said venom.

9. The method of claim 1 wherein said sample comprises blister fluid.

10. The method of claim 1 wherein said *Loxosceles* spider is a *Loxosceles Reclusa*.

11. The method of claim 1 wherein said detecting is performed using an ELISA modified to reduce blocking antibodies using nonfat milk solids and alkaline phosphatase markers.

12. The method of claim 11 wherein said ELISA is capable of identifying under 24 picograms of venom in a sample.

13. The method of claim 1 wherein said sample is exposed to ambient summertime temperatures for up to about three weeks prior to said detecting.

14. The method of claim 1 wherein said detecting distinguishes said organism from other species of venomous organism.

* * * * *